US007238367B2

(12) United States Patent
Tardi et al.

(10) Patent No.: US 7,238,367 B2
(45) Date of Patent: Jul. 3, 2007

(54) LIPOSOME LOADING WITH METAL IONS

(75) Inventors: Paul Tardi, Surrey (CA); Sharon Johnstone, Vancouver (CA); Murray Webb, Vancouver (CA); Marcel Bally, Bowen Island (CA); Sheela Abraham, Vancouver (CA)

(73) Assignee: Celator Pharmaceuticals, Inc., Princeton, NJ (US)

( * ) Notice: Subject to any disclaimer, the term of this patent is extended or adjusted under 35 U.S.C. 154(b) by 580 days.

(21) Appl. No.: 10/264,818

(22) Filed: Oct. 3, 2002

(65) Prior Publication Data

US 2003/0091621 A1    May 15, 2003

Related U.S. Application Data

(60) Provisional application No. 60/394,273, filed on Jul. 9, 2002, provisional application No. 60/362,074, filed on Mar. 7, 2002, provisional application No. 60/356,759, filed on Feb. 15, 2002, provisional application No. 60/341,529, filed on Dec. 17, 2001, provisional application No. 60/326,671, filed on Oct. 3, 2001.

(51) Int. Cl.
*A61K 9/127* (2006.01)

(52) U.S. Cl. .................. 424/450; 264/4.1; 264/4.3

(58) Field of Classification Search .............. 424/450; 264/4.1, 4.3, 4.6
See application file for complete search history.

(56) References Cited

U.S. PATENT DOCUMENTS

| 3,932,657 A | 1/1976 | Rahman ................... 424/319 |
| 5,010,073 A | 4/1991 | Kappas et al. ............. 514/185 |
| 5,227,170 A * | 7/1993 | Sullivan .................... 424/450 |
| 5,616,341 A | 4/1997 | Mayer et al. ............... 424/450 |
| 5,663,387 A | 9/1997 | Singh ......................... 554/80 |
| 5,744,158 A | 4/1998 | Mayer et al. ............... 424/450 |
| 5,795,589 A | 8/1998 | Mayer et al. ............... 424/450 |
| 5,837,282 A | 11/1998 | Fenske et al. .............. 424/450 |
| 6,045,821 A | 4/2000 | Garrity et al. ............. 424/450 |
| 6,083,530 A | 7/2000 | Mayer et al. ............... 424/450 |
| 6,274,116 B1 | 8/2001 | Hawthorne et al. ........ 424/1.21 |

FOREIGN PATENT DOCUMENTS

| DE | 41 34 158 | 4/1993 |
| DE | 43 41 479 | 6/1995 |
| WO | WO 93/26019 | 12/1993 |
| WO | WO 94/13265 | 6/1994 |
| WO | WO 99/59545 | 11/1999 |
| WO | WO 01/85131 | 11/2001 |
| WO | WO 01/89653 | 11/2001 |

OTHER PUBLICATIONS

Saxon et al in Journal of Liposome Research 9 (4), pp. 507-522 (1999).*
Borle et al. "$Ca^{2+}$ Binding to Phosphatidylglycerol Bolayers as Studied by Differential Scanning Calorimetry and $^2$H- d $^{31}$P-Nuclear Magnetic Resonance" Chemistry and Physics of Lipids 36:263-283 (1985).
Bouma, J et al. "Anthracycline Antitumour Agents- A Review of Physiocochemical, Analytical and Stability Properties" Pharm. Weekl. Sci. Edn. 16:109-133 (1986).
Cheung et al. "Loading of Doxorubicin into Liposomes by Forming $MN^{2+}$Drug Complexes" Biochimica et Biophysica Acta 1414:205 (1998).
Deamer et al. "Catecholamine Uptake and Concentration by Liposomes Maintaining pH Gradients" Biochimica et Biophysica Acta 455:269-271 (1976).

(Continued)

*Primary Examiner*—Gollamudi S. Kishore
(74) *Attorney, Agent, or Firm*—Morrison & Foerster LLP

(57) ABSTRACT

This invention relates to encapsulation of drugs and other agents into liposomes.

13 Claims, 24 Drawing Sheets

OTHER PUBLICATIONS

Fenske et al. "Ionophore-Mediated Uptake of Ciprofloxacin and Vincristine into Large Unilamellar Vesicles Exhibiting Transmembrane Ion Gradients" Biochim. Biophys. Acta 1414:188-204 (1998).

Jacobson et al. "Phase Transitions and Phase Separations in Phospholipid Membranes Induced by Changes in Temperature, pH, and Concentration of Bivalent Cations" Biochemistry 14(1):152-161 (1975).

Mayer et al. "Uptake of Adriamycin into Large Unilamellar Vesicles in Response to a Ph Gradient" Biochimica et Biophysica Acta 857:123 (1986).

Needham et al. "PEG-Covered Lipid Surfaces: Bilayers and Monolayers" Colloids and Surfaces B: Biointerfaces 18:183-195 (2000).

Riley, CM et al. "Characterization of the Complexation of Fluoroquinolone Antimicrobials with Metal Ions by Nuclear Magnetic Resonance Spectroscopy" J. Pharm. Biomed. Anal. 11:49-59 (1993).

Steffan et al. "Divalent Cation-Dependent Interaction of Sulfated Polysaccharides with Phosphatidylcholine and Mixed Phophatidylcholine/Phosphatidylglycerol Liposomes" Chem. Phys. Lipids 74(2):141-150 (1994).

\* cited by examiner

LIPOSOME LOADING WITH METAL IONS

CROSS-REFERENCE TO RELATED APPLICATIONS

This application claims benefit under 35 U.S.C. § 119(e) of provisional applications U.S. Ser. No. 60/326,671 filed 3 Oct. 2001; Ser. No. 60/341,529 filed 17 Dec. 2001; Ser. No. 60/356,759 filed 15 Feb. 2002; Ser. No. 60/362,074 filed 7 Mar. 2002 and Ser. No. 60/394,273 filed 9 Jul. 2002. The contents of these applications are incorporated herein by reference.

TECHNICAL FIELD

This invention relates to encapsulation of drugs and other agents into liposomes.

BACKGROUND OF THE INVENTION

Liposomes are microscopic particles that are made up of one or more lipid bilayers enclosing an internal compartment. Liposomes can be categorized into multilamellar vesicles, multivesicular liposomes, unilamellar vesicles and giant liposomes. Multilamellar liposomes (also known as multilamellar vesicles or "MLV") contain multiple concentric bilayers within each liposome particle, resembling the "layers of an onion". Multivesicular liposomes consist of lipid membranes enclosing multiple non-concentric aqueous chambers. Liposomes that enclose a single internal aqueous compartment include small unilamellar vesicles (SUVs) and large unilamellar vesicles (LUVs). LUVs and SLVs range in size from about 50 to 500 nm and 20 to 50 nm respectively. Giant liposomes typically range in size from 5000 nm to 50,000 nm and are used mainly for studying mechanochemical and interactive features of lipid bilayer vesicles in vitro (Needham et al., Colloids and Surfaces B: Biointerfaces (2000) 18: 183–195).

Liposomes have been widely studied and used as carriers for a variety of agents such as drugs, cosmetics, diagnostic reagents, and genetic material. Since liposomes consist of non-toxic lipids, they generally have low toxicity and therefore are useful in a variety of pharmaceutical applications. In particular, liposomes are useful for increasing the circulation lifetime of agents that have a short half-life in the bloodstream. Liposome-encapsulated drugs often have biodistributions and toxicities which differ greatly from those of free drug. For specific in vivo delivery, the sizes, charges and surface properties of these carriers can be changed by varying the preparation methods and by tailoring the lipid makeup of the carrier. For instance, liposomes may be made to release a drug more quickly by decreasing the acyl chain length of a lipid making up the carrier.

Liposomes containing metal ions encapsulated in the interior of the vesicle have been used in diagnostic applications. For example, liposomes have been used for delivery of contrast agents with the goal of accumulating a contrast agent at a desired site within the body of a subject. In the latter application, liposomes have mainly been used for delivery of diagnostic radionucleotides and paramagnetic metal ions in gamma and magnetic resonance imaging, respectively. This includes liposomal encapsulation of radionucleotides such as $^{111}$In, $^{99m}$Tc and $^{67}$Ga and paramagnetic ions such as Gd, Mn and manganese oxide. Two methods are typically employed to prepare liposomes for imaging purposes. In the first method, the metal is converted to a soluble chelate and then introduced into the aqueous interior of a liposome. In the second method, a chelating agent derivatized with a lipophilic group is anchored to the liposome surface during or after liposome preparation.

Manganese and non-transition metal ions have also been involved in methods for encapsulation of ionizable agents into liposomes containing an ionophore inserted in the liposome membrane (see U.S. Pat. No. 5,837,282 and Fenske et al., Biochim. Biophys. Acta (1998) 1414: 188–204). In this method, the ionophore translocates the metal ion across the liposome membrane in exchange for protons, thereby establishing a pH gradient. The establishment of an appropriate pH gradient across the liposome bilayer allows the ionizable agent to be encapsulated since the agent can readily cross the liposomal bilayer in the neutral form and subsequently become encapsulated and trapped within the aqueous interior of the liposome due to conversion to the charged form (see Mayer et al., U.S. Pat. Nos. 6,083,530, 5,616,341, 5,795,589 and 5,744,158; Mayer et al., Biochimica et Biophysica Acta (1986) 857:123). This work arose from mechanistic studies completed by Deamer et al., (Biochimica et Biophysica Acta (1976) 455:269–271) who demonstrated that liposomes efficiently concentrated several catecholamines (dopamine, norepinephrine and epinephrine) in response to a transmembrane pH gradient).

The presence of an acidic liposomal interior and a basic to neutral exterior environment allows agents that are primarily in the neutral form at neutral to basic pH and primarily in the charged form at acidic pH to be readily entrapped within a liposome. Drugs containing ionizable moieties such as amine groups are readily encapsulated and retained in liposomes containing an acidic interior. This method, where an ionophore (A23187) is used to generate a pH gradient across a manganese-containing liposome, has been used to load topotecan into cholesterol-free liposomes comprising a PEG-lipid conjugate inserted in the membrane (see WO/0185131). However, successful loading and retention using a transmembrane pH gradient is realized while the internal pH of the liposome is maintained. Since the pH gradient can only be maintained for short periods of time, clinical formulation of drugs into liposomes requires the generation of a pH gradient in liposomes just prior to drug loading. A second disadvantage of this method results from instability of lipid, and some drugs, at acidic pH which prevents the need for long-term storage of the drug loaded liposome. Freezing of liposomal formulations slows the rate of hydrolysis but conventional liposomal formulations often aggregate and leak contents upon thawing unless appropriately selected cryoprotectants are used.

Complexes between drugs such as doxorubicin or ciprofloxacin and divalent metal ions such as $Mn^{2+}$ have been reported (Bouma, J., et al. (1986) Pharm. Weekbl. Sci. Edn. 16:109–133; Riley, C. M., et al. (1993) J. Pharm. Biomed. Anal. 11:49–59; and, Fenske, D. B. (1998) Biochim. Biophys. Acta. 1414:188–204). Recently, it was reported that uptake of doxorubicin (but not ciprofloxacin) into sphingomyelin/cholesterol LUVs could be carried out with manganese in the internal loading medium without the presence of an ionophore (Cheung et al., Biochimica et Biophysica Acta (1998) 1414:205). It was suggested that a process involving both complex formation between doxorubicin and manganese ions and protonation of doxorubicin inside the liposome resulted in uptake of this particular drug in the presence of manganese ions. Stable entrapment of doxorubicin was reported but this work relied on the use of sphingomyelin/cholesterol liposomes, a formulation noted for optimal drug retention. The methodology reported by Cheung, et al., involving the use of MnSO$_4$ in pH 7.4 HEPES buffer is not reproducible because the metal precipitates from such a buffer.

Various groups have investigated the interaction of metal ions with liposomes with the goal of evaluating the effects of metal cations on vesicle membranes (Steffan et al. (1994) Chem. Phys. Lipids 74(2): 141–150). Divalent metal cations such as Ca$^{2+}$ have been implicated in the unfavourable formation of metal induced crosslinking of phosphatidylglycerol (PG) containing liposomes due to the negative charge of the liposome surface. Metal ions have also been implicated in increasing the phase transition temperature of negatively modeled membrane systems (Borle, et al., (1985) Chemistry and Physics of Lipids 36: 263–283; Jacobson, et al., (1975) Biochemistry 14(1): 152–161). These studies revealed that the addition of calcium to dipalmitoylphosphatidylglycerol (DPPG) membranes resulted in a phase transition temperature increase by about 50° C. These results indicate that the use of negatively charged lipids in conjunction with metal ions will result in liposomes that exhibit inferior characteristics for in vivo applications.

SUMMARY OF THE INVENTION

This invention is based on the discovery that liposome loading efficiency and retention properties using metal-based procedures carried out in the absence of an ionophore in the liposome is surprisingly dependent on the metal employed and the lipid makeup of the liposome. By selecting lipid makeup and a metal composition, loading or retention properties can be tailored to achieve a desired loading or release of a selected agent from a liposome. Furthermore, undesirable precipitation of metal from solutions employed in formulating metal ion encapsulated liposomes may be avoided by use of metal compatible solutions, and loading may also be enhanced by rigorous removal or complexation of metal ions from an external solution containing such liposomes.

This invention thus provides a method of loading an agent into a liposome, comprising preparing a liposome containing an encapsulated metal, the liposome being present in an external solution; and, adding to the external solution an agent such that said agent is encapsulated in the liposome providing that if an agent encapsulated into the liposome is doxorubicin, the encapsulated metal is not solely manganese. In one embodiment of this aspect of the invention, the encapsulated metal is a transition metal. Preferably there will be little or no pH difference between the interior and exterior of the liposome. More preferred, the pH will be comparable to the pH of physiological fluids or an approximately neutral pH. Preferably, the external solution will have less, more preferably substantially less of the metal. Preferably, the external solution and the surface of the liposomes will be essentially free of the metal in an uncomplexed state. Additionally, the present invention provides compositions which are prepared according to this mhe present invention thus also provides methods for loading agents into liposomes, comprising the steps of:

i) preparing a liposome comprising an encapsulated transition metal ion and, ii) adding to the external solution of said liposome, an agent such that said agent is encapsulated in the liposome.

The transition metal ion may be selected from one or more of Fe, Co, Ni, Cu, Zn, V, Ti, Cr, Rh, Ru, Mo and Pd and may be encapsulated in a liposome in which Mn is also encapsulated.

The present invention provides compositions which are prepared according to this method as well as liposomes containing a transition metal ion or two or more different such ions, suitable for use in the method.

The invention also provides a method of loading liposomes using a metal ion in a "metal compatible" solution as described herein to minimize precipitation of the metal and to maintain it in solution for sufficient time to prepare the liposome. The present invention thus also encompasses a method of loading an agent into a liposome, said method comprising the steps of:

i) preparing a liposome having an encapsulated medium comprising a metal ion and a metal compatible solution;

ii) adding to the external solution of said liposome, an agent such that said agent is encapsulated in the liposome.

Additionally, the present invention provides compositions which are prepared according to this method as well as liposomes containing a metal ion and metal compatible solutions suitable for use in this method.

Preferably, after drug encapsulation, a liposome of this invention or used in methods of this invention has an extraliposomal pH that is substantially similar to the intraliposomal pH. More preferably, the extraliposomal and intraliposomal pH is at about pH 3.5 to pH 9.0, more preferably, it is between about pH 6.0 to pH 8.5, even more preferably, it is between about 6.5 and 8.5, and most preferably, it is between about pH 6.5 and pH 7.5.

This invention is further based on the finding that liposomes prepared to be of low cholesterol content display unexpected loading and retention properties when metal-based loading is utilized. Thus, the present invention also provides a method for encapsulating an agent into a liposome, the liposome being present in an external solution, said method comprising the steps of:

i) preparing a liposome comprising:
   a) one or more vesicle forming lipids, providing that the liposome is of low cholesterol;
   b) an encapsulated metal in a metal compatible solution;

ii) adding to the external solution an active agent such that the agent is encapsulated into the liposome.

In one embodiment of this aspect of the invention, the metal compatible solution includes a transition metal.

In another aspect of the invention, the present invention provides a method for encapsulating an agent into a liposome, the method comprising the steps of:

i) providing a liposome of this invention in an external solution, wherein the liposome does not have a transmembrane pH gradient;

ii) adding to the external solution, an agent such that the agent is encapsulated into the liposome.

Furthermore, this invention also relates to methods of administering liposomes to a mammal and methods of treating a mammal affected by or susceptible to or suspected of being affected by a disorder (e.g. cancer). In particular, the invention encompasses a method of administering a liposome to a subject comprising administering a pharmaceutical composition comprising liposomes of the invention. Methods of treatment or of administration will generally be understood to comprise administering the pharmaceutical composition at a dosage sufficient to ameliorate said disorder or symptoms thereof. In one aspect, this invention is based on the finding that liposomes loaded with active agent using an encapsulated metal display loading and retention properties that are distinct from that displayed by manganese.

This invention provides a liposome composition comprising a liposome containing an internal solution comprising one or more encapsulated transition metal ions and one or more therapeutic agents, providing that if the liposome has a lipid composition consisting of sphingomyelin and cholesterol or if the one or more therapeutic agents is solely doxorubicin, the one or more encapsulated ions is not solely manganese. This invention also provides the aforementioned liposome composition wherein the liposomes are in an external solution.

This invention also provides a method of loading liposomes with an agent, wherein the liposome composition is a liposome composition as described above, the method comprising: selecting an agent that is capable of crossing membranes of liposomes in the composition when present in the external solution of the composition but incapable of crossing said membranes when in a complex with the one or more metal ions in the internal solution, adding the selected agent to the external solution of the composition, and maintaining the agent in the external solution for sufficient time to load the agent.

This invention also provides methods for preparing, selecting or designing liposomes, comprising selecting a metal ion for encapsulation in a liposome to achieve a desired retention of an encapsulated agent in the liposome. Thus, a method for providing, preparing or selecting a liposome composition having a preferred loading or retention property for a selected agent according to this invention may comprise:

a) providing a first liposome composition as described above;
b) adding the selected agent to the external solution of the composition of (a) for a time sufficient to provide for loading of the agent into liposomes of the composition;
c) providing a second liposome composition as described above;
d) adding the selected agent to the external solution of the composition of (c) for a time sufficient to provide for loading of the agent into liposomes of the composition;
e) comparing amount of agent loaded or agent retention for liposomes of the composition resulting at (b) to liposomes of the composition resulting at (d); and
f) selecting, providing, or preparing the liposome composition resulting at (b) or (d) having a preferred loading or retention, wherein the liposome composition of (a) and (c) differ by one or more of: (i) metal ions present in the internal solution; (ii) lipids in the liposomes of the liposome composition; iii) time and/or temperature conditions sufficient to provide for loading of the agents; and iv) the concentration of metal ions present in the internal solution.

DETAILED DESCRIPTION OF THE INVENTION

Preparation of Liposomes

Figure 1A:
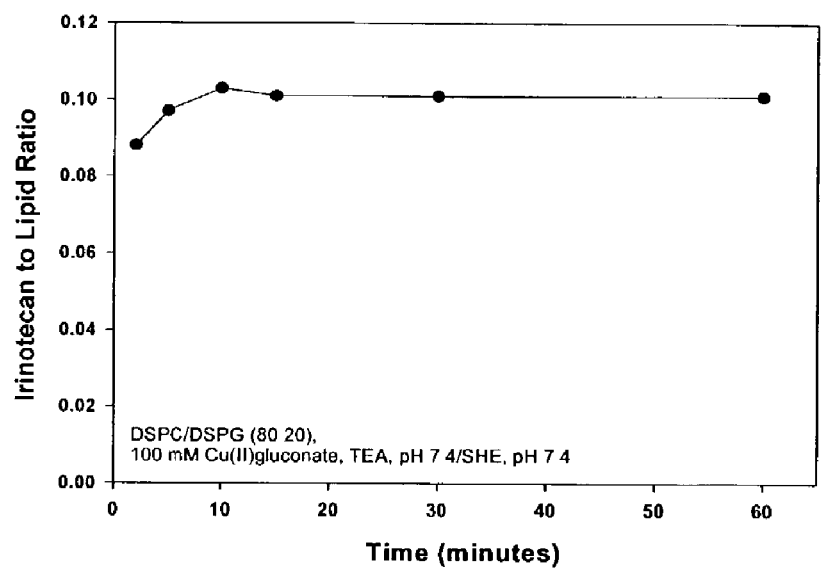
FIG. 1A: A graph showing loading of irinotecan into DSPC/DSPG (80:20 mole ratio) liposomes as a function of time using 100 mM Cu(II)gluconate buffered to pH 7.4 with triethanolamine (TEA) as the internal medium and 300 mM sucrose, 20 mM HEPES, 30 mM EDTA (SHE), pH 7.4 as the external medium. Loading was carried out at 50° C. at a drug-to-lipid mole ratio of 0.1:1.

The term "liposome" as used herein means vesicles comprised of one or more concentrically ordered lipid bilayers encapsulating an aqueous phase. Formation of such vesicles requires the presence of "vesicle-forming lipids" which are amphipathic lipids capable of either forming or being incorporated into a bilayer structure. The latter term includes lipids that are capable of forming a bilayer by themselves or when in combination with another lipid or lipids. An amphipathic lipid is incorporated into a lipid bilayer by having its hydrophobic moiety in contact with the interior, hydrophobic region of the membrane bilayer and its polar head moiety oriented toward an outer, polar surface of the membrane. Hydrophilicity arises from the presence of functional groups such as hydroxyl, phosphato, carboxyl, sulfato, amino or sulfhydryl groups. Hydrophobicity results from the presence of a long chain of aliphatic hydrocarbon groups.

It will be appreciated that any suitable vesicle-forming lipid may be utilized in the practice of this invention as judged by one of skill in the art. This includes phospholipids such as phosphatidylcholine (PC), phosphatidylglycerol (PG), phosphatidylinositol (PI), phosphatidic acid (PA), phosphatidyethanolamine (PE) and phosphatidylserine (PS); glycolipids; and sphingolipids such as sphingosine, ceramides, sphingomyelin, and glycosphingolipids (such as cerebrosides and gangliosides). Preferred phospholipids comprise two acyl chains from 6 to 24 carbon atoms selected independently of one another and with varying degrees of unsaturation.

Liposomes prepared in accordance with this invention can be generated by conventional techniques used to prepare vesicles. These techniques include the ether injection method (Deamer et al., Acad. Sci. (1978) 308: 250), the surfactant method (Brunner et al., Biochim. Biophys. Acta (1976) 455: 322), the freeze-thaw method (Pick et al., Arch. Biochim. Biophys. (1981) 212: 186) the reverse-phase evaporation method (Szoka et al., Biochim. Biophys. Acta. (1980) 601: 559–71), the ultrasonic treatment method (Huang et al., Biochemistry (1969) 8: 344), the ethanol injection method (Kremer et al., Biochemistry (1977) 16: 3932), the extrusion method (Hope et al., Biochim. Biophys. Acta (1985) 812:55–65) and the french press method (Barenholz et al., FEBS Lett. (1979) 99: 210). All of the above processes are basic technologies for the formation of liposome vesicles and these processes can be used in combinations. Preferably, small unilamellar vesicles (SUVs) are prepared by the ultrasonic treatment method, the ethanol injection method and the French press method. Preferably, multilamellar vesicles (MLVs) are prepared by the reverse-phase evaporation method or by the simple addition of an aqueous solution to a lipid film followed by dispersal by mechanical agitation (Bangham et al., J. Mol. Biol. (1965) 13: 238–252).

Particularly suitable liposome preparations which may be used in the practice of this invention are large unilamellar vesicles (LUVs). LUVs may be prepared by the ether injection method, the surfactant method, the freeze-thaw method, the reverse-phase evaporation method, the french press method or the extrusion method. Preferably, LUVs are prepared according to the extrusion method. The extrusion method involves first combining lipids in chloroform to give a desired mole ratio. A lipid marker may optionally be added to the lipid preparation. The resulting mixture is dried under a stream of nitrogen gas and placed in a vacuum pump until the solvent is substantially removed. The samples are then hydrated in an appropriate aqueous solution, which may contain a mixture of therapeutic agent or agents. The mixture is then passed through an extrusion apparatus (e.g. apparatus by Northern Lipids, Vancouver, Canada) to obtain liposomes of a defined size. Average liposome size can be determined by a variety of methods including quasi-elastic light scattering using, for example, a NICOMP™ 370 submicron particle sizer at a wavelength of 632.8 nm.

In some aspects of this invention, liposomes are prepared to be of "low-cholesterol". Such liposomes contain "substantially no cholesterol," or "essentially no cholesterol." The term "substantially no cholesterol" allows for the presence of an amount of cholesterol that is insufficient to significantly alter the phase transition characteristics of the liposome (typically less than 20 mol % cholesterol). 20 mol % or more of cholesterol broadens the range of temperatures at which phase transition occurs, with phase transition disappearing at higher cholesterol levels (e.g. greater than 30 mol %). Preferably, a liposome having substantially no cholesterol will have about 15 or less and more preferably about 10 or less mol % cholesterol. The term "essentially no cholesterol" means about 5 or less mol %, preferably about 2 or less mol % and even more preferably about 1 or less mol % cholesterol. Most preferably, no cholesterol will be present or added when preparing "low cholesterol" liposomes.

Liposomes of this invention may comprise a hydrophilic polymer-lipid conjugate such as a polyalkylether-lipid conjugate. Grafting a hydrophilic polymer such as a polyalkylether to the surface of liposomes has been utilized to "sterically stabilize" liposomes thereby increasing the circulation longevity of liposomes. This results in enhanced blood stability and increased circulation time, reduced uptake into healthy tissues, and increased delivery to disease sites such as solid tumors (see: U.S. Pat. Nos. 5,013,556 and 5,593,622; and Patel et al., Crit Rev Ther Drug Carrier Syst (1992) 9: 39–90). Typically, the polymer is conjugated to a lipid component of the liposome. The term "hydrophilic polymer-lipid conjugate" refers to a vesicle-forming lipid covalently joined at its polar head moiety to a hydrophilic polymer, and is typically made from a lipid that has a reactive functional group at the polar head moiety in order to attach the polymer. Suitable reactive functional groups are for example, amino, hydroxyl, carboxyl or formyl groups. The lipid may be any lipid described in the art for use in such conjugates. Preferably, the lipid is a phospholipid having two acyl chains comprising between about 6 to about 24 carbon atoms in length with varying degrees of unsaturation. Most preferably, the lipid in the conjugate is a PE, preferably of the distearoyl form. The polymer is a biocompatible polymer characterized by a solubility in water that permits polymer chains to effectively extend away from a liposome surface with sufficient flexibility that produces uniform surface coverage of a liposome. Preferably, such a polymer is a polyalkylether, including polyethylene glycol (PEG), polymethylene glycol, polyhydroxy propylene glycol, polypropylene glycol, polylactic acid, polyglycolic acid, polyacrylic acid and copolymers thereof, as well as those disclosed in U.S. Pat. Nos. 5,013,556 and 5,395,619. Preferably, such a polymer has a molecular weight between about 350 and 5000 daltons. The conjugate may be prepared to include a releasable lipid-polymer linkage such as a peptide, ester, or disulfide linkage. The conjugate may also include a targeting ligand. Mixtures of conjugates may be incorporated into liposomes for use in this invention.

Negatively charged lipids as described below may be incorporated in metal encapsulated liposome formulations to increase the circulation longevity of the carrier. These lipids may be employed in place of hydrophilic polymer lipid conjugates as surface stabilizing agents. Embodiments of this invention may make use of cholesterol-free liposomes containing such negatively charged lipids to prevent aggregation thereby increasing the blood residence time of the carrier. Such embodiments are ideally loaded following rigorous removal of metal ions from the surface of the liposome and the external solution of the liposomes.

The term "negatively charged lipid" refers to a vesicle-forming lipid having one or more negative charges at physiological pH, including phospholipids and sphingolipids. Negatively charged lipids may be incorporated in a liposome of this invention at 5 to 95 mol %, more preferably at 10 to 50 mol % and most preferably at 15 to 30 mol %.

Preferably, a lipid that is negatively charged at physiological pH for use in this invention will comprise a "non-zwitterionic moiety" which refers to a moiety that does not have opposing charges at physiological pH. Such lipids impart to the liposome desirable circulation properties for in vivo uses. The net negative charge on the lipid may arise solely from the presence of the negative charge on the lipid (e.g. from a phosphate group) or where the lipid has more than one charge, additional negative charge may be due to the presence of a negatively charged non-zwitterionic moiety. Preferably, however, the negative charge arises solely from the lipid component in which case the non-zwitterionic moiety is a neutral group. Preferably, the non-zwitterionic comprises 2 to 6 carbon atoms.

Suitable non-zwitterionic moieties contain electron-withdrawing functional groups that impart to the head group hydrophilic characteristics. Such functional groups can be selected from the group consisting of alcohols, acids, ketones, esters, ethers, amides and aldehydes. Non-zwitterionic moieties of the following formulas may be utilized:

Alcohols
P—R or POR or PO(CH$_2$)$_2$NHR where R is —(CH$_2$)$_v$(CH)$_w$(C)$_x$(OH)$_y$(CH$_3$)$_z$
  wherein the number of carbons (v+w+x+z) is 2–6 most preferably 3–5
  where the number of OH groups is 1–3 (y=1–3)
  e.g. DPPG Ketones
P—R or POR or PO(CH$_2$)$_2$NHR where R is —(CH$_2$)v(C)x(CO)y(CH$_3$)z
  where the number of carbons (v+x+y+z) is 2–6 most preferably 3–5
  where the number of ketone groups is 1–2 (y=1–2)
  e.g. N-butyryl-DPPE, N-valeryl-DPPE Carboxylic Acids
P—R or POR or PO(CH$_2$)$_2$NHR where R is —(CH$_2$)$_u$(CH)$_v$(C)$_x$(COOH)$_y$(CH$_3$)$_z$
  where the number of carbons (u+v+x+y+z) is 2–6 most preferably 3–5
  where the number of carboxylic acid groups is 1–2 (y=1–2)

Esters
P—R or POR or PO(CH$_2$)$_2$NHR where R is —(CH$_2$)$_v$(C)$_x$(COO)$_y$(CH$_3$)$_z$
  where the number of carbons (v+x+y+z) is 2–6 most preferably 3–5
  where the number of ester groups is 1–2 (y=1–2)

Ethers
P—R or POR or PO(CH$_2$)$_2$NHR where R is —(CH$_2$)$_v$(C)$_x$(O)$_y$(CH$_3$)$_z$
  where the number of carbons (v+x+z) is 2–6 most preferably 3–5
  where the number of ether groups is 1–2 (y=1–2)

Amines

Primary Amines:
P—R or POR or PO(CH$^2$)$_2$NHR where R is —(CH$_2$)$_v$(C)$_w$(CH)$_x$(NH$_3$)$_y$(CH$_3$)$_z$
  where the number of carbons (v+w+x+z) is 2–6 most preferably 3–5
  where the number of amino groups is 1–2 (y=1–2)

Secondary Amines:
P—R or POR or PO(CH$_2$)$_2$NHR where R is —(CH$_2$)$_v$(C)$_w$(CH)$_x$(NH$_2$)$_y$(CH$_3$)$_z$
  where the number of carbons (v+w+x+z) is 2–6 most preferably 3–5
  where the number of amine groups is 1–2 (y=1–2)

Tertiary Amines:
P—R or POR or PO(CH$_2$)$_2$NHR where R is —(CH$_2$)$_v$(CH)$_w$(C)$_x$(N)$_y$(CH$_3$)$_z$
  where the number of carbons (v+w+x+z) is 2–6 most preferably 3–5
  where the number of amine groups is 1(y=1)

The non-zwitterionic moiety may also be comprised of combinations of functional groups; for example a compound of formula:

Carboxylic Acids and Ketones
P—R or POR or PO(CH$_2$)$_2$NHR where R is —(CH$_2$)$_u$(CH)$_v$(C)$_w$(COOH)$_x$(CO)$_y$(CH$_3$)$_z$
  where the number of carbons (u+v+w+x+y+z) is 2–6 most preferably 3–5
  where the number of carboxylic acid groups is 1–2 (x=1–2)
  where the number of ketone groups is 1–2 (y=1–2)
  e.g. N-succinyl-DPPE, N-glutaryl-DPPE
P—R or POR or PO(CH$_2$)$_2$NHR where R is —(CH$_2$)$_s$(CH)$_t$(C)$_u$(COOH)$_v$(CO)$_x$(OH)$_y$(CH$_3$)$_z$ Carboxylic Acids, Ketones and Alcohols
  where the number of carbons (s+t+u+v+x+z) is 2–6 most preferably 3–5
  where the number of carboxylic acid groups is 1–2 (v=1–2)
  where the number of ketone groups is 1–2 (x=1–2)

where the number of hydroxyl groups is 1–2 (y=1–2) e.g. N-tartaryl-DPPE

Ring Structures

P—R or POR or PO(CH$_2$)$_2$NHR where R is a 5 or 6 member ring containing 1–5 or 1–6 alcohol groups (cyclitols), respectively (e.g. phosphatidylinositol).

Carbohydrates

Monosaccharides that may be used in the practice of this invention include arabinose, fucose, galactose, glucose, lyxose, ribose and xylose. Disaccharides include sucrose, lactose, trehalose, cellobiose, gentiobiose and maltose. For purposes of extending the circulation lifetime of the liposome, monosaccharides and disaccharides which do not bind to cellular receptors are preferred (e.g. mannose).

In the case where the non-zwitterionic moiety is neutral, the head group consists of groups that are neutral at physiological pH including alcohols, ketones, esters, ethers, amides and aldehydes.

In preferred embodiments of the invention, the non-zwitterionic moiety is a short-chain alcohol, a preferred alcohol containing two or more hydroxyl groups. The alcohol can be a straight-chain polyol of which glycerol is an example. Glycerol may make up the head group of a phosphosphingolipid or a phospholipid through linkage of one of the hydroxyl groups to the phosphate group of the lipid. Most preferably, glycerol is attached to the phosphate via a terminal hydroxyl group of the glycerol molecule, the resulting molecule being termed phosphatidylglycerol (PG). Preferably the fatty acid chains of the phosphatidylglycerol are selected independently of each other from the group consisting of caproyl (6:0), octanoyl (8:0), capryl (10:0), lauroyl (12:0), myristoyl (14:0), palmitoyl (16:0), stearoyl (18:0), arachidoyl (20:0), behenoyl (22:0), lingnoceroyl (24:0) and phytanoyl, including the unsaturated versions of these fatty acid chains in the cis or trans configurations such as oleoyl (18:1), linoleoyl (18:2), arachidonoyl (20:4) and docosahexaenoyl (22:6). Phospholipids having two acyl chains of 14 to 18 carbon atoms are preferred.

In another preferred embodiment of the invention, the non-zwitterionic moiety is a ring structure. Most preferably the ring structure is a cyclitol, which is a cycloalkane containing one hydroxyl group on each of three or more ring atoms. Such compounds may be derivatized with various groups to impart to the molecule a desired water solubility. Preferably the cyclitol is an inositol attached to a phospholipid through the phosphate group, the resulting compound being phosphatidylinositol (PI). Preferably, the fatty acid chains of the phosphatidylinositol are selected independently of each other from the group consisting of caproyl (6:0), octanoyl (8:0), capryl (10:0), lauroyl (12:0), myristoyl (14:0), palmitoyl (16:0), stearoyl (18:0), arachidoyl (20:0), behenoyl (22:0), lingnoceroyl (24:0) and phytanoyl, including the unsaturated versions of these fatty acid chains in the cis or trans configurations such as oleoyl (18:1), linolcoyl (18:2), arachidonoyl (20:4) and docosahexaenoyl (22:6). Phosphatidylinositol having two acyl chains of 14 to 18 carbon atoms are preferred.

Negatively charged lipids may be obtained from natural sources or may be chemically synthesized. Methods to covalently attach compounds to the head group of a lipid are well known in the art and generally involve reacting functional groups on the terminal portion of the lipid head group with functional groups on the moiety to be attached. Suitable lipids for the chemical attachment of a hydrophilic moiety include lipids having a polar head group that terminates with a reactive functional group such as an amine or a carboxylic acid. An example of a particularly suitable lipid is phosphatidylethanolamine as it contains a reactive amino group. Methods for preparing phosphatidylethanolamine derivatives have been described in Ahl, P., et al. (1997) Biochimica et Biophysica Act 1329: 370–382, the reference of which is incorporated herein by reference. Examples of negatively charged lipids obtained from natural sources include phosphatidylglycerol and phosphatidylinositol obtained from egg and plant sources respectively.

Encapsulation of Active Agents and Metals in Liposomes

This invention provides a method for loading an agent into a liposome comprising an encapsulated transition metal. Within this specification, the term "agent" refers to substances which are capable of being encapsulated into liposomes according to this invention. Preferably, such an agent will be a "therapeutic agent" capable of exerting an effect on a target, in vitro or in vivo. Suitable active agents include, for example, prodrugs, diagnostic agents, therapeutic agents, pharmaceutical agents, drugs, synthetic organic molecules, proteins, peptides, vitamins, steroids and steroid analogs. The agent, at least when not complexed with a transition metal, must be permeable across a liposomal membrane in order to achieve loading.

Transition metals for use in this invention include the Group 1B, 2B, 3B, 4B, 5B, 6B, 7B and 8B elements (groups 3–12). Preferred metals include those selected from the group consisting of Fe, Co, Ni, Cu, Zn, V, Ti, Cr, Rh, Ru, Mo, Mn and Pd. More preferably, the metal is Fe, Co, Ni, Cu, Mn or Zn. Even more preferably, the metal is Zn, Mn, Co or Cu. Even more preferably, the metal is Zn, Co, or Cu.

Transition metal ions used in accordance with this invention may be encapsulated in liposomes according to conventional techniques known in the art. This includes the passive encapsulation techniques known in the art and as described below.

Preferably, the liposomes are formed in a solution comprising a transition metal at a concentration of from about 20 mM to about 1 M, preferably from about 50 mM to about 800 mM and more preferably from about 100 to about 350 mM.

Various salts of metals may be employed in the practice of this invention. Preferably, the salt is pharmaceutically acceptable and soluble in aqueous solvent. Preferred salts may be selected from the group consisting of chlorides, sulfates, tartrates, citrates, phosphates, nitrates, carbonates, acetates, glutamates, gluconates, glycinates, histidinates, lysinates and the like.

Preferably, a therapeutic agent to be encapsulated into a liposome of this invention is one which is capable of coordinating with a metal encapsulated in the liposome. Agents that are capable of coordinating with a transition metal typically comprise coordination sites such as amines, carbonyl groups, ethers, ketones, acyl groups, acetylenes, olefins, thiols, hydroxyl, halides, groups or other suitable groups capable of donating electrons to the transition metal thereby forming a complex with the metal. Examples of agents which bind transition metals and thus may be used in the practice of this invention include quinolones such as fluoroquinolones, quionlones such as nalidixic acid, anthracyclines such as doxorubicin, daunorubicin idarubicin and epirubicin, amino glycosides such as kanamycin and other antibiotics such as bleomycin, mitomycin C and tetracycline and nitrogen mustards such as cyclophosphamide, thiosemicarbazones, indomethacin and nitroprusside, camptothecins such as topotecan, irinotecan, lurtotecan, 9-aminocamptothecin, 9-nitrocamptothecin and 10-hydroxycamptothecin and, podophyllotoxins such as etoposide. Agents used in this invention can be capable of donating electrons from different atoms in the agent and to different sites in the geometric structure of the complex. Such agents capable of donating more than one non-bonding pair of electrons are also known as multidentate. Preferably a therapeutic agent for use in this invention is an antineoplastic agent.

Non-limiting examples of active agents that complex with transition metals and thus may be used in the practice of this invention are provided in Table I.

TABLE I

EXAMPLES OF METAL-BASED ACTIVE AGENTS

| METAL(S) | AGENT(S) | REFERENCE |
|---|---|---|
| Cu | etoposide | Tawa et al. (1997) Biol. Pharm. Bull. 20: 1002–1005 |
| Fe (III) | dexrazoxane, losoxantrone, piroxantrone | Hasinoff et al. (1999) Journal of Inorganic Biochemistry 77: 257–259 |
| Zn, Cu(II), Fe(III), Co(III) | bleomycin | Wenbao et al. (2001) Biochemistry 40: 7559–7568 |
| Fe(III) | anthracyclines | Fiallo et al. (1999) Journal of Inorganic Biochemistry 75: 105–115 |
| Bi(III) | quinolones | Turel et al. (1997) Journal of Inorganic Biochemistry 66: 241–245 |
| Cu(II) | L-lysine L-arginine | Chikira et al. (1997) Journal of Inorganic Biochemistry 66: 131–139 |
| Cu(II), Ni(II), Zn(II), Mo(VI) | desferrioxamine B | Farkas et al. (1997) Journal of Inorganic Biochemistry 65: 281–286 |
| Cu(II) | cynnamyl derivative of rafamycin | Bontchev et al. (1997) Journal of Inorganic Biochemistry 65: 175–182 |
| Fe(III) | adriamycin | Capolongo et al. (1997) Journal of Inorganic Biochemistry 65: 115–122 |
| Cu(II), Ni(II) | cinoxacin | Ruiz et al. (1997) Journal of Inorganic Biochemistry 65: 87–96 |

Methods of determining whether coordination occurs between an agent and a transition metal include conventional techniques well know to those of skill in the art. Preferred techniques involve measuring the absorption spectra or using NMR as described by Greenaway and Dabrowiak (J. Inorg. Biochem. (1982) 16(2): 91). If desired, an active agent may be tested before encapsulation in order to determine whether coordination occurs and the optimal pH for complexation.

A preferred technique for preparing liposomes with an encapsulated metal involves first combining lipids in chloroform to give a desired mole ratio. A lipid marker may optionally be added to the lipid preparation. The resulting mixture is dried under a stream of nitrogen gas and placed in a vacuum pump until the solvent is removed. Subsequently, the samples are hydrated in a solution comprising a transition metal (which may comprise more than one metal, for example Cu and Mn, or one metal, but different salts of the metal). The mixture is then passed through an extrusion apparatus to obtain a preparation of liposomes of a defined size. Average liposome size can be determined by quasi-elastic light scattering using a NICOMP™ 370 submicron particle sizer at a wavelength of 632.8 nm. Subsequent to extrusion, the external solution may be treated or replaced so as to remove metal ions from the external solution and the liposome surface.

This invention preferably makes use of liposomes with an encapsulated or "internal" medium comprising a transition metal in a "metal compatible solution". Use of a metal compatible solution prevents precipitation of the metal or minimizes precipitation to an extent sufficient to allow for pharmaceutical use of the liposomes.

A metal compatible solution is defined as one that consists of a metal in solution that does not cause unacceptable precipitation to occur for at least the time required to formulate liposomes. Preferably, the metal solution should be clear and soluble, free of aggregation, precipitation or flocculation for at least about 4 hours. By way of example, a 300 mM solution of $MnSO_4$ in pH 7.4 HEPES buffer as described in Cheung, et al. [supra] is not a metal compatible solution as it produces an obvious brown precipitate of $Mn(OH)2$ comprising approximately 6–7 molar % of the manganese added to the solution.

Various methods are known in the art and may be used to determine if the metal solution is forming a precipitate such as centrifugation of the solution and an evaluation of whether a pellet is formed or observation of cloudiness in the solution. The absorbance of the solution can also be monitored by spectroscopy (e.g. increase in absorbance at 690 nm), where a substantial increase in absorbance is indicative of solution instability and precipitation. The simplest method is to filter the solution and look for the presence of a precipitate on the filter. For example, a 50 ml sample may be passed through Whatman(tm) No. 2 filter paper and the filter observed for visible sediment.

A preferred method to determine whether a solution is metal compatible is to monitor absorbance at 690 nm. Additional of metal should not result in an increase of more than about 0.1 absorption units and preferably no more than about 0.05 units.

An alternative preferred method of determining whether a metal solution is metal compatible is by centrifugation (e.g. 100 ml sample at 1000 rpm for 10 minutes) to collect any precipitate, measuring the amount of precipitate collected and determining the proportion of the metal added to the original solution present in the precipitate. The amount of metal in the precipitate should not exceed about 1 molar % of the amount of metal added to the original solution.

Preferred metal compatible solutions are those that are also pharmaceutically acceptable such as ones comprising triethanolamine (TEA), sodium chloride, sodium acetate/acetic acid, sodium citrate/citric acid or sugars such as sucrose, dextrose and lactose. Phosphate and carbonate based solutions (although pharmaceutically acceptable) will have limited use except at pH's outside of normal physiological ranges, due to the likelihood of metal precipitation. Preferably, the metal compatible solution is buffered and has pH in a physiological range.

In the practice of this invention, it may be advantageous for the external solution of the liposome preparation to be replaced or be treated in order that the resulting external solution contain substantially no uncomplexed metal ions prior to loading of an agent. For purposes of this specification, "uncomplexed metal ions" includes metal ions free in the external solution and metal ions bound to (or otherwise associated with) the external surface of the liposomes. Conversely, a complexed metal ion is one which is no longer free to interact with the therapeutic agent or the liposome surface because it is present in the external solution in a complex with a moiety such as a chelating agent. Thus, it is preferable that the surface of the liposomes and the external solution be substantially free of the metal ions or if metal ions are present, that they be complexed with a chelating agent. Examples of cationic chelating agents that may be employed include: EDTA and derivatives; EGTA and derivatives; histidine; Chelex(tm); TPEN and derivatives; BAPTA and derivatives; bisphosphonate; o-phenanthrolene (phenanthroline); citrate; InsP6; Diazo-2; and DTPA (diethylene-triaminopenta acetic acid) isothiocyanate.

Replacement of the external solution to remove metal ions can be accomplished by various other techniques, such as by chromatography of the liposome preparation through an extensive gel filtration column equilibrated with a second aqueous buffered solution, by centrifugation, extensive or repeated dialysis, exchange of the external medium, treating the external solution with chelating agents or by related techniques. A single solution exchange or round of dialysis without the use of a chelating agent is typically insufficient to remove metal ions from the surface of negatively charged liposomes.

The external solution is also preferably a buffered solution. However, it is appreciated that any suitable solvent may be utilized in the practice of this invention. A preferred external solution has a pH at about physiological pH and comprises a buffer which has a buffering range to include physiological pH. Non-limiting examples of suitable buffers for the external solution are HBS, pH 7.4 (150 mM NaCl, 20 mM HEPES) and SHE, pH 7.4 (300 mM sucrose, 20 mM HEPES, 30 mM EDTA).

Uptake of an agent may be established by incubation of the mixture at a suitable temperature after addition of the agent to the external medium. Depending on the composition of the liposome, temperature and pH of the internal medium, and chemical nature of the agent, uptake of the agent may occur over a time period of minutes or hours. Loading may be carried out at temperatures of, for example, 20° C. to about 75° C., preferably from about 30° C. to about 60° C.

Removal of unencapsulated agent may be carried out by passing a liposome preparation through a gel filtration column equilibrated with a second aqueous buffered solution, or by centrifugation, dialysis, or related techniques. Preferably, the second solution is one that is physiologically compatible but need not be "metal compatible". After removal of unencapsulated active agent, the extent of agent loading may be determined by measurement of drug and lipid levels according to conventional techniques. Lipid and drug concentrations may be determined by employing techniques such as scintillation counting, spectrophotometric assays, fluorescent assays and high performance liquid chromatography. The choice of analysis depends on the nature of the drug and whether the liposomes contain a radiolabeled lipid marker. An example of quantification utilizing a radiolabeled marker is set forth in the Examples herein, although it will be appreciated that any suitable method of determining the extent of loading may be used.

Prior to loading of an agent into a liposome using an encapsulated transition metal, the liposome may be passively co-encapsulated with an agent and a metal. Using this approach, two or more agents may be incorporated into the liposome by combining passive and active methods of loading.

Subsequent to loading of an agent into a liposome, an ionophore may be incubated with the mixture such that insertion of the ionophore into the bilayer occurs. The term "ionophore" refers to a compound which forms a complex with a metal ion and assists the ion in crossing a lipid bilayer while further assisting the transport of H+ in the counter direction. Examples of suitable ionophores for the present invention include nigericin, monensin, dianemycin, A23187, 4-BrA23187, ionomycin and X-537A. The ionophores may be specific for monovalent or divalent metal ions. Examples of ionophores specific for monovalent metal ions include nigericin, monensin and dianemycin. Uptake of the ionophore is established by addition of the ionophore to the mixture and incubation at a temperature suitable for incorporation of the ionophore into the liposomal bilayer. The amount of ionophore used will typically depend on the nature and type of liposome formulation. Addition of the ionophore to the liposome after loading of the agent may be carried out in order to subsequently impose a pH gradient across the liposomal bilayer to alter the retention properties of the agent in the liposome or to protect agents that are affected by neutral or alkaline environments such as, topotecan and irinotecan.

Preferred metal compatible solutions may include components such as buffers that can be utilized between pH 6.0 and 8.5. Preferably, the buffer does not substantially precipitate over a two-day time period at 4° C. with an encapsulated metal ion at pH 6.0 to 8.0 and more preferably pH 6.5 to 7.5. A buffer may be tested for its ability to prevent precipitation by visually inspecting the solution for the appearance of cloudiness, which is indicative of formation of a precipitate. An example of a method for determining whether a buffer is compatible with a particular transition metal is outlined in Example 3. After encapsulation of a transition metal in a metal compatible solution, an agent may be added to the external medium such that the agent is encapsulated into the liposome. Liposomes encapsulating a transition metal and a metal compatible solution may be prepared according to conventional techniques known in the art including the techniques described above. It is appreciated, however, that any suitable metal may be utilized in this aspect of the invention. Preferably, the liposome with the encapsulated agent or agents has an extraliposomal pH that is substantially similar to the intraliposomal pH. Most preferably, the extraliposomal and intraliposomal pH is about pH 6.0 to pH 8.0, most preferably, it is between about pH 6.5 and pH 7.5.

The present invention further provides a method of designing liposomes, said method comprising selecting a metal ion for encapsulation in a liposome to achieve a desired retention of an encapsulated agent. It will be appreciated that any suitable liposome and agent may be utilized in the practice of this aspect of the invention. Other preferred features and conditions of this aspect of the invention are as generally described above.

In order to determine the rate of release of an agent from a liposome, the liposome may be administered intravenously and plasma levels of agent and lipid measured after administration. For example, the lipid component may be radioactively labeled and the plasma subjected to liquid scintillation counting. The amount of drug may be determined by a spectrophotometric, HPLC or other assays. Similarly, testing for the retention of the agent in the liposome may be carried out in vitro in plasma or a suitable buffer. By way of example, a liposome comprising an encapsulated agent and transition metal may be tested in vitro or in vivo for retention of agent. If a desired retention of the agent is not achieved, a different metal may be selected and tested for its ability to retain the agent of interest.

Administering Liposomes

This invention also relates to methods of administering liposomes to a mammal, and methods of treating a mammal affected by or susceptible to or suspected of being affected by a disorder (e.g. cancer). Methods of treatment or of administration will generally be understood to comprise administering the pharmaceutical composition at a dosage sufficient to ameliorate said disorder or symptoms thereof.

For treatment of human ailments, a qualified physician may be expected to determine how the compositions of the present invention should be utilized with respect to dose, schedule and route of administration using established protocols. Such applications may also utilize dose escalation should active agents encapsulated in delivery vehicle compositions of the present invention exhibit reduced toxicity to healthy tissues of the subject.

Preferably, the pharmaceutical compositions are administered parenterally, i.e., intraarterialy, intravenously, intraperitoneally, subcutaneously, or intramuscularly or via aerosol. Aerosol administration methods include intranasal and pulmonary administration. More preferably, the pharmaceutical compositions are administered intravenously or intraperitoneally by a bolus injection or infusion. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. Particular formulations which are suitable for this use are found in Remington's Pharmaceutical Sciences, Mack Publishing Company, Philadelphia, Pa., 17th ed. (1985).

EXAMPLES

The following examples are given for the purpose of illustration and are not by way of limitation on the scope of the invention. Unless otherwise specified, pH was adjusted using triethanolamine (TEA) and results shown in the drawings are from a single representative example.

Methods for Preparation of Large Unilamellar Liposomes

Lipids were dissolved in chloroform solution and subsequently dried under a stream of nitrogen gas and placed in a vacuum pump to remove solvent. Unless otherwise specified, trace levels of radioactive lipid 3H—CHE were added to quantify lipid during the formulation process. The resulting lipid film was placed under high vacuum for a minimum of 2 hours. The lipid film was hydrated in the solution indicated to form multilamellar vesicles (MLVs). The resulting preparation was extruded 10 times through stacked polycarbonate filters with an extrusion apparatus (Lipex Biomembranes, Vancouver, BC) to achieve a mean liposome size between 80 and 150 nm. All constituent lipids of liposomes are reported in mole %.

Methods for Quantification of Drug Loading

At various time points after initiation of drug loading, aliquots were removed and passed through a Sephadex G-50 spin column to separate free from encapsulated drug. To a specified volume of eluant, Triton X-100 or N-ocyl beta-D-glucopyranoside (OGP) was added to solubilize the liposomes. Following addition of detergent, the mixture was heated to the cloud point of the detergent and allowed to cool to room temperature before measurement of the absorbance or fluorescence. Drug concentrations were calculated by comparison to a standard curve. Lipid levels were measured by liquid scintillation counting.

Example 1

Metal Loading Can Occur in the Absence of a pH Gradient

Metal-containing liposomes with internal and external solutions buffered to pH 7.4 were investigated for their ability to load drug. These studies were performed to determine whether metal-based loading of drug could occur independently of the presence of a pH gradient. Conventional techniques for actively loading drugs into liposomes often require the presence of a transmembrane pH gradient.

In order to determine whether copper loading of irinotecan in the absence of a pH gradient could occur using a cholesterol-free formulation, DSPC/DSPG (80:20 mole ratio) liposomes containing copper(II)gluconate were prepared with an external and internal pH of 7.4. Lipid films of DSPC/DSPG at a mole ratio of 80:20 were prepared as described above in the method section. The lipid films were hydrated in 100 mM Cu(II)gluconate adjusted to pH 7.4 with triethanolamine (TEA) and extruded at 70° C. The liposomes were buffer exchanged into 300 mM sucrose, 20 mM HEPES, 30 mM EDTA (SHE buffer), pH 7.4 by tangential flow dialysis and subsequently washed three times in 6 mL of SHE, pH 7.4 to remove any copper(II)gluconate from the extraliposomal solution. Irinotecan was added to the liposome preparation at a 0.1:1 drug-to-lipid mole ratio and incubated at 50° C. The extent of drug loading was determined as described in the methods by measuring absorbance at 370 nm and lipid levels were determined by liquid scintillation counting.

Results depicted in FIG. 1A show that loading of irinotecan into DSPC/DSPG (80:20 mole ratio) liposomes with no pH gradient at 50° C. was essentially complete within about 5 minutes after initiation of loading.

Loading of daunorubicin into DSPC/DSPG (90:10 mole ratio) liposomes containing encapsulated $CuSO_4$ buffered to pH 7.4 was also investigated. Lipid films were prepared according to the methods except DSPG was dissolved in chloroform/methanol/water (50:10:1 v/v). A solution of 150 mM $CUSO_4$, 20 mM histidine (adjusted to pH 7.4 using TEA), was employed as the hydration medium and MLVs were extruded at 70° C. The liposomes were exchanged into SHE, pH 7.4 using a hand-held tangential flow dialysis column. Daunorubicin was loaded at a 0.1:1 drug/lipid weight ratio. A drug-to-lipid ratio at various time points during loading was determined by measuring absorbance at 480 nm after solubilization in detergent to quantify daunorubicin as described; lipid levels were determined by liquid scintillation counting.

Figure 1B:
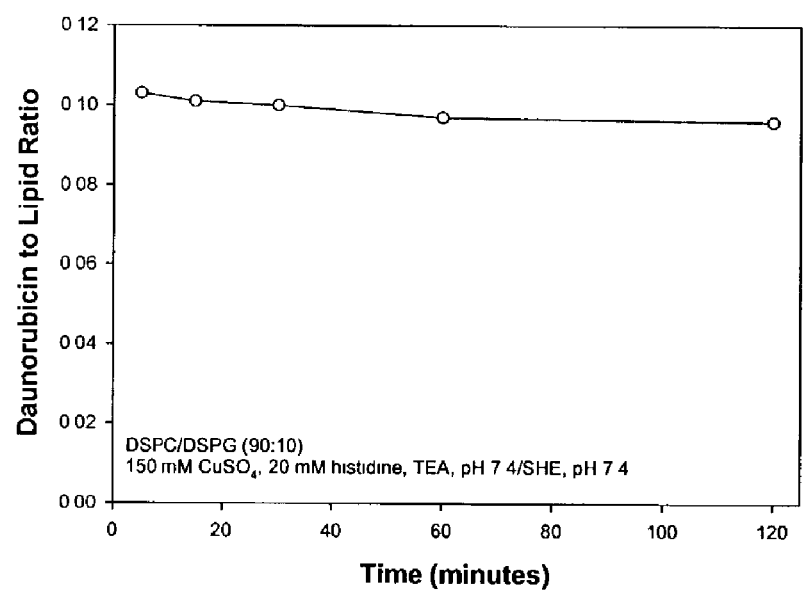
FIG. 1B: A graph showing loading of daunorubicin into DSPC/DSPG (90:10 mole ratio) liposomes as a function of time using 150 mM $CuSO_4$, 20 mM histidine adjusted to pH 7.4 with TEA as the internal medium and SHE, pH 7.4 as the external medium. Loading was carried out at 60° C. at a drug-to-lipid weight ratio of 0.1:1.

As summarized in FIG. 1B, uptake of daunorubicin into DSPC/DSPG (90:10 mole ratio) liposomes in the absence of a pH gradient was 100% at all time points measured.

Copper loading of irinotecan into cholesterol-containing liposomes exhibiting no pH gradient was investigated employing DPPC/Chol (55:45 mole ratio) liposomes. The liposomes were prepared as described in the methods by hydrating lipid films in a solution of 100 mM copper(II) gluconate adjusted to pH 7.4 with TEA. Liposomes were extruded at 65° C. and the external buffer of the liposomes was exchanged to SHE, pH 7.4 by tangential flow dialysis. Liposomes were incubated with irinotecan at a 0.1:1 drug-to-lipid weight ratio at 50° C. and the extent of drug loading was determined as described by measuring absorbance at 370 nm after solubilization by detergent.

Figure 2:
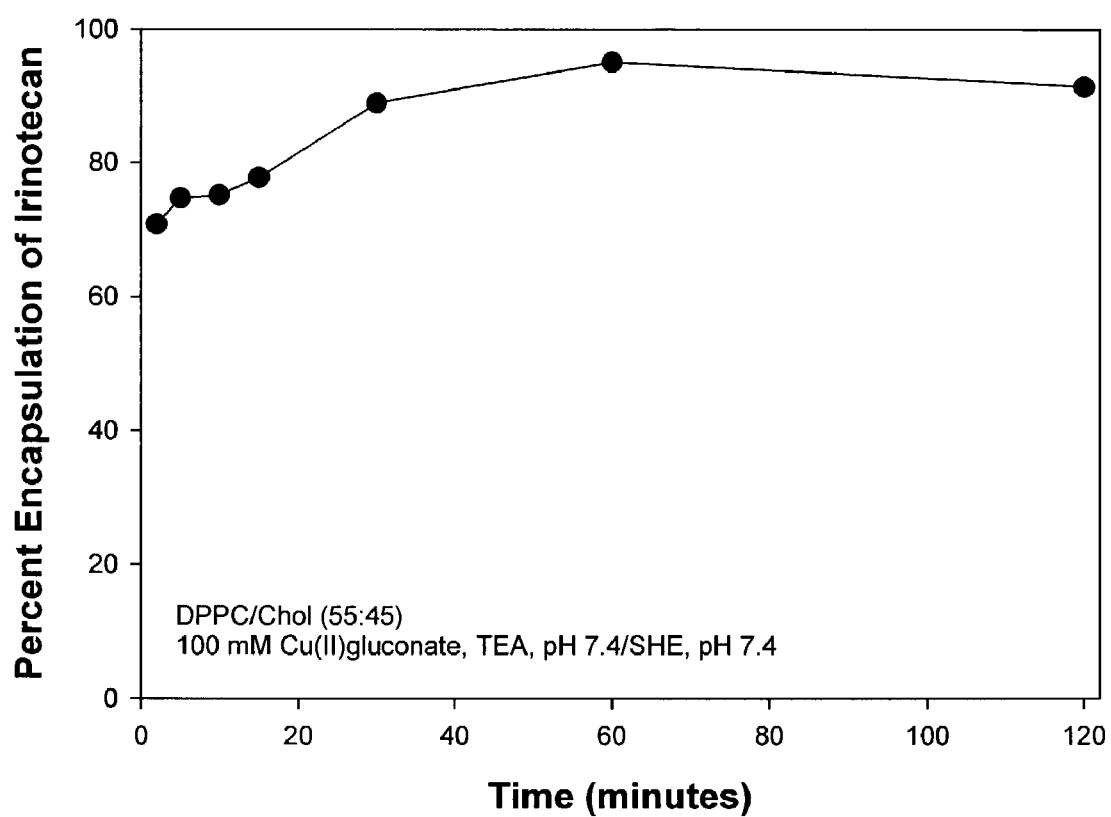
FIG. 2: A graph showing loading of irinotecan into DPPC/Chol (55:45 mole ratio) liposomes as a function of time using 100 mM Cu(II)gluconate adjusted to pH 7.4 with TEA as the internal medium and SHE, pH 7.4 as the external medium. Loading was carried out at 50° C. at a drug-to-lipid weight ratio of 0.1:1.

Loading of irinotecan into DPPC/Chol (55:45 mole ratio) liposomes in the absence of a pH gradient revealed that almost complete loading was observed after about 60 minutes of incubation (FIG. 2).

In addition to copper loading, loading of drug using $MnSO_4$ containing liposomes in the absence of a pH gradient was also investigated. DSPC/DSPE-PEG2000 (95:5 mole ratio) liposomes were prepared with an internal $MnSO_4$ solution buffered to pH 7.4 and an external solution buffered to pH 7.4 with SHE. Lipids films were prepared as described and hydrated in 300 mM $MnSO_4$ buffered to pH 7.4 with 20 mM imidazole (initial pH was adjusted to 7.4 with concentrated HCl) and extrusion was carried out at 70° C. The samples were run down a Sephadex G-50 column to exchange the exterior buffer with SHE, pH 7.4. Epirubicin was loaded at a drug-to-lipid weight ratio of 0.2:1 and loading was carried out at 60° C. The extent of drug loading was measured as described in the methods by measuring drug absorbance at 480 nm.

Figure 3:
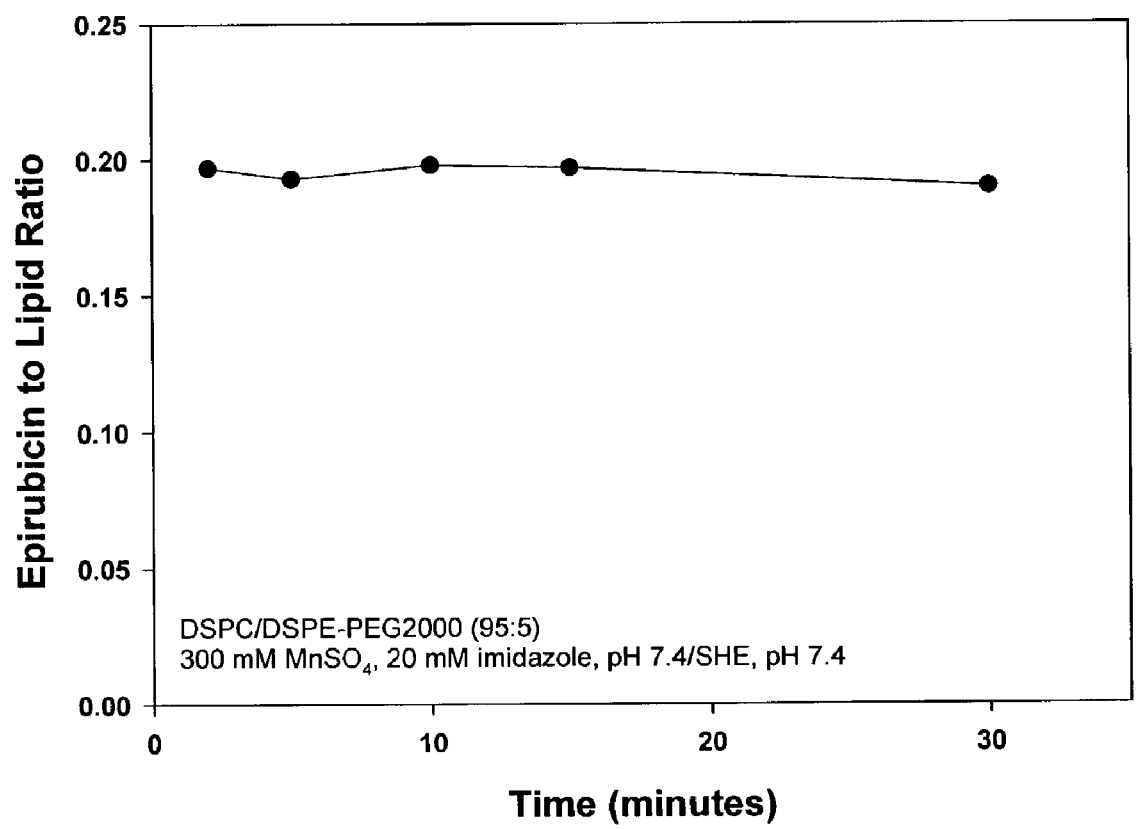
FIG. 3: A graph showing loading of epirubicin into DSPC/DSPE-PEG2000 (95:5 mole ratio) liposomes as a function of time using 300 mM $MnSO_4$, 20 mM imidazole, pH 7.4 as the internal medium and SHE, pH 7.4 as the external medium. Loading was carried out at 60° C. at a drug-to-lipid weight ratio of about 0.2:1.

Results summarized in FIG. 3 reveal that manganese loading of epirubicin into DSPC/DSPE-PEG2000 (95:5 mole ratio) liposomes at 60° C. does not require the presence of a pH gradient as efficient encapsulation of drug occurred at each time point measured.

Example 2

Metal Loading of a Second Drug into Buffered Liposomes Containing a Passively Encapsulated First Drug Although the above examples describe the metal-induced loading of one drug into liposomes, the technique can be employed to load two or more drugs into a single liposome. One technique involves first passively entrapping at least one drug along with a metal during preparation of the liposome followed by active metal loading of another drug. In this example, liposomes were prepared such that there was no pH gradient across the membrane thus ensuring loading of the second drug by the process of this invention.

Loading of irinotecan into DSPC/DSPG and DSPC/Chol/DSPG liposomes, containing passively encapsulated floxuridine (FUDR), was investigated using various conditions as well as loading of irinotecan into carboplatin-containing liposomes and daunorubicin loading into cisplatin-containing liposomes.

DSPC/DSPG (85:15 mole ratio) liposomes containing FUDR were prepared by dissolving DSPC in chloroform and DSPG in chloroform/methanol/water (50:10:1 v/v). The lipids were then combined together at an 85:15 mole ratio and labeled with trace amounts of 14C—CHE. The samples were hydrated in 100 mM copper(II)gluconate, 220 mM TEA, pH 7.4, containing 24.62 mg/mL (100 mM) FUDR with trace levels of 3H-FUDR at 70° C. The resulting MLVs were extruded at 70° C., then buffer exchanged first into saline and next into SHE, pH 7.4 using a hand-held tangential flow dialysis column. This sample was then exchanged into 300 mM sucrose, 20 mM HEPES, pH 7.4 to remove any EDTA in the exterior buffer.

Irinotecan was added to the resulting liposome preparation at a drug-to-lipid mole ratio of 0.1:1 at 50° C. A drug-to-lipid ratio for the spun column eluant was generated using liquid scintillation counting to determine lipid and FUDR concentrations, and absorbance at 370 nm to determine irinotecan concentrations. Prior to measurement of absorbance, liposomes were solubilized in a solution containing Triton X-100. The initial FUDR drug-to-lipid mole ratio was 0.09:1, and 0.06:1 after loading of irinotecan occurred.

Figure 4A:
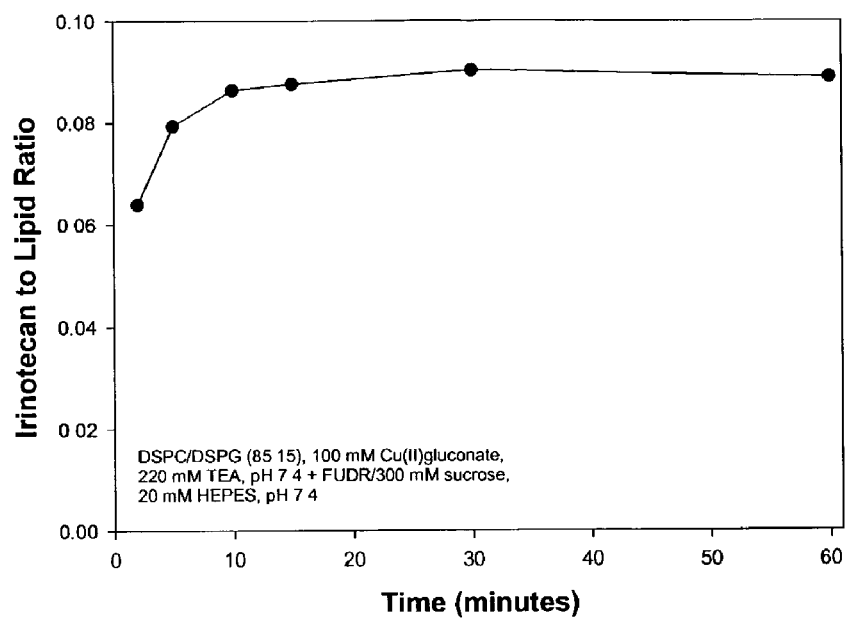
FIG. 4A: A graph showing loading of irinotecan into floxuridine (FUDR) containing DSPC/DSPG liposomes at an 85:15 mole ratio as a function of time using 100 mM Cu(II)gluconate, 220 mM TEA, pH 7.4 as the internal medium and 300 mM sucrose, 20 mM HEPES, pH 7.4 as the external solution. FUDR was passively encapsulated and irinotecan loading was carried out at 50° C. at a drug-to-lipid mole ratio of 0.1:1.

FIG. 4A shows that loading of irinotecan into cholesterol-free DSPC/DSPG (85:15 mole ratio) liposomes containing encapsulated FUDR and metal does not require the presence of a pH gradient as efficient loading of the drug occurred throughout the time course of the experiment.

DSPC/Chol/DSPG (70:10:20 mole ratio) liposomes containing FUDR and copper(II)gluconate were prepared as described above. To measure the effects of external buffer on loading, half of the resulting LUVs were buffer exchanged into SHE, pH 7.4 and then into 20 mM HEPES, 150 mM NaCl (HBS), pH 7.4 while the other half was further exchanged into 300 mM sucrose, 20 mM HEPES, pH 7.4 using a hand-held tangential flow dialysis column. Irinotecan was added to the FUDR-containing liposomes, and subsequently measured, as described above. The initial FUDR drug-to-lipid mole ratios were 0.1:1 and 0.09:1 for samples respectively containing HBS (closed circles) or 300 mM sucrose, 20 mM HEPES (open circles) as the external buffer. After loading of irinotecan, the same samples had FUDR drug/lipid ratios of 0.09:1 and 0.08:1, respectively.

Figure 4B:
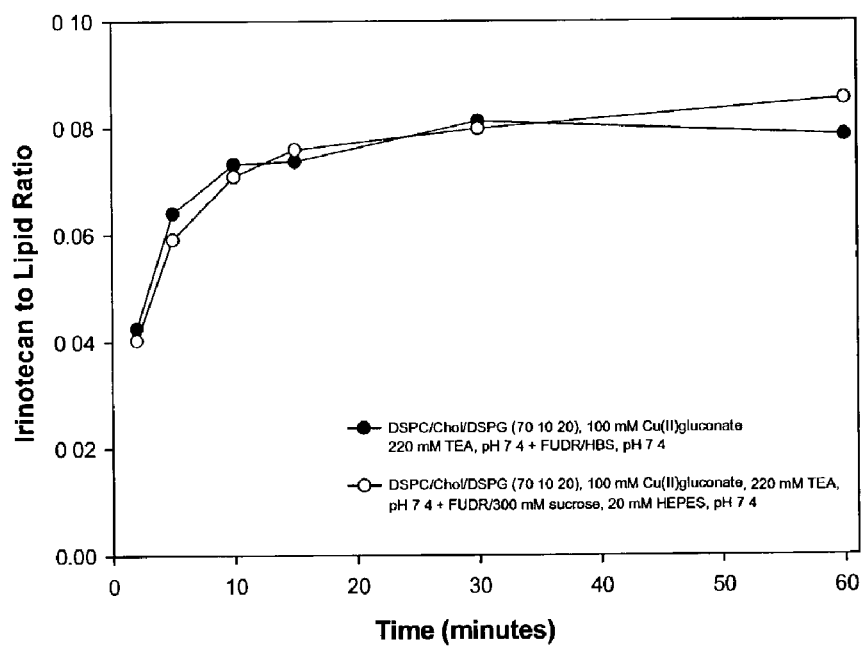
FIG. 4B: A graph showing loading of irinotecan into FUDR-containing DSPC/Chol/DSPG (70:10:20 mole ratio) liposomes as a function of time using 100 mM Cu(II) gluconate, 220 mM TEA, pH 7.4 as the internal medium and either 20 mM HEPES, 150 mM NaCl (HBS), pH 7.4 (●) or 300 mM sucrose, 20 mM HEPES, pH 7.4 (○) as the external buffer. FUDR was passively encapsulated and irinotecan loading was carried out at 50° C. at a drug-to-lipid mole ratio of 0.1:1.

Results summarized in FIG. 4B show that irinotecan efficiently loads into low cholesterol-containing liposomes with encapsulated FUDR regardless of the external buffer employed. Loading in the absence of a pH gradient further supports that this degree of irinotecan uptake occurs through the metal loading technique of this invention.

We have also shown various other drugs capable of metal loading in the absence of a pH gradient into liposomes containing passively encapsulated drug; examples are detailed as follows:

Loading of irinotecan into DSPC/DSPG (80:20 mole ratio) liposomes with passively encapsulated carboplatin was measured using liposomes prepared as described above except that lipid films were hydrated in 150 mM $CUSO_4$ (adjusted to pH 7.4 using TEA), containing 25 mg/ml carboplatin. Samples were extruded and external buffers exchanged into SHE, pH 7.4, using a hand-held tangential flow dialysis column. Irinotecan was added at 60° C. at a drug-to-lipid weight ratio of 0.1:1 and uptake was measured as previously described. Atomic absorption spectrometry (AA) was used to determine carboplatin concentrations and absorbance at 370 nm was measured to determine irinotecan concentrations. The initial carboplatin drug-to-lipid weight ratio was 0.030, and 0.025 after loading of irinotecan occurred.

Figure 5:
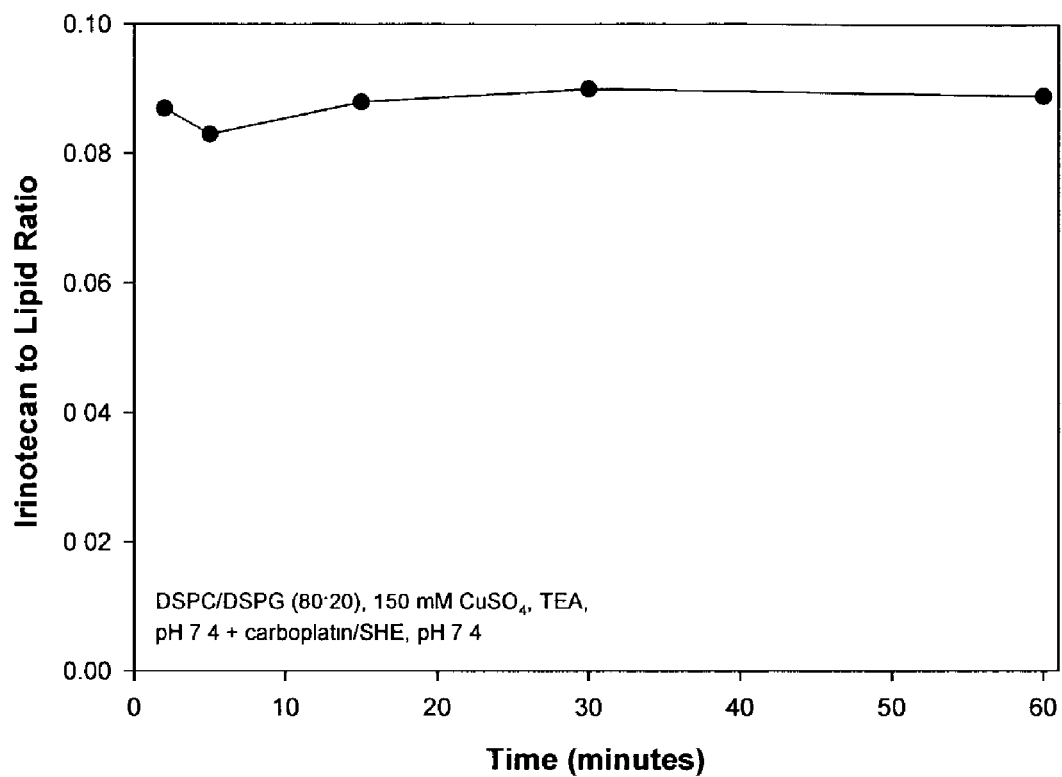
FIG. 5: A graph showing loading of irinotecan into carboplatin-containing DSPC/DSPG (80:20 mole ratio) liposomes as a function of time using 150 mM $CuSO_4$ adjusted to pH 7.4 with TEA as the internal medium and SHE, pH 7.4 as the external buffer. Carboplatin was passively encapsulated and irinotecan loading was carried out at 60° C. at a drug-to-lipid weight ratio of 0.1:1.

As seen in the graph of FIG. 5, irinotecan loads to a high degree in carboplatin and metal-containing DSPC/DSPG (80:20 mole ratio) liposomes in the absence of a pH gradient.

To measure loading of daunorubicin into liposomes containing encapsulated cisplatin, DSPC/Chol (55:45 mole ratio) liposomes were prepared as described for FIG. 4B except that lipid films were hydrated with a cisplatin solution. Solid Cisplatin (40 mg/mL) was dissolved in 150 mM $CuCl_2$, pH 7.4 (pH adjusted with NaOH) with the addition of 4% DMSO at 80° C. then added to the lipid films and allowed to hydrate at 80° C. with frequent vortexing. Upon cooling, the samples were centrifuged on a bench top centrifuge to pellet any unencapsulated cisplatin, and the supernatant collected. The liposomes were then applied to a Sephadex G-50 column pre-equilibrated with HBS, pH 7.4 to remove excess metal ions from the outside of the liposomes.

Daunorubicin was added to the liposomes at a 0.1:1 weight ratio and loading was carried out at 60° C. Aliquots were removed at various time points and applied to a Sephadex G-50 spin column. Absorbance measurements were carried out at 480 nm was used to determine daunorubicin concentrations and cisplatin levels were measured using AA. The initial cisplatin drug-to-lipid ratio was 0.044:1.

Figure 6:
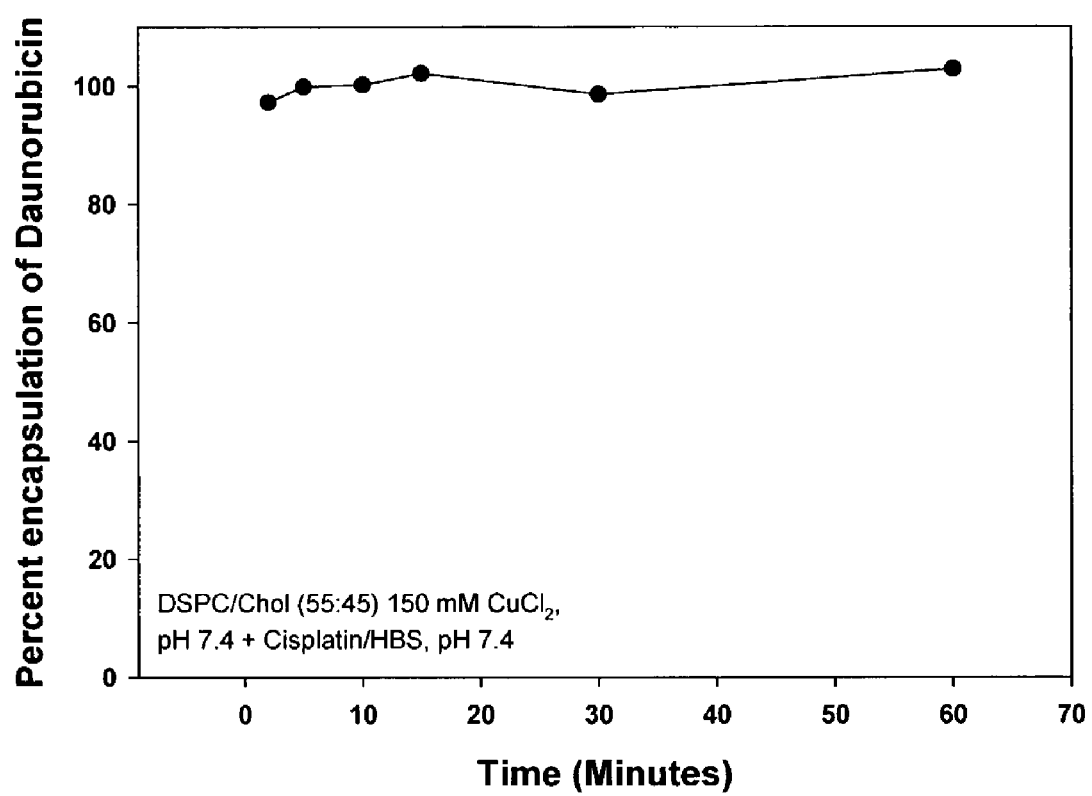
FIG. 6: A graph showing loading of daunorubicin into cisplatin-containing DSPC/Chol (55:45 mole ratio) liposomes as a function of time using 150 mM $CuCl_2$ adjusted to pH 7.4 with NaOH as the internal medium and HBS, pH 7.4 as the external medium. Cisplatin was passively encapsulated and daunorubicin loading was carried out at 60° C. at a drug-to-lipid weight ratio of 0.1:1.

FIG. 6 shows that DSPC/Chol liposomes containing passively encapsulated cisplatin efficiently load daunorubicin in the absence of a pH gradient. This further supports loading of a second agent, into liposomes, through metal loading complexation.

Example 3

The Effect of Buffer Composition on the Precipitation of Metal Ion

Solutions of cobalt, nickel, manganese, cadmium, zinc and copper were prepared at concentrations of 150 and 300 mM in 20 mM histidine. Triethanolamine (1.13 g/mL) was added drop-wise until the resulting solution was pH 7.4 or until the solution was cloudy in appearance (over a 10 minute observation period). Typically, less than 500 (L of 1.13 g/mL triethanolamine was added. Subsequent to addition of triethanolamine, the solutions were visually inspected to determine whether precipitation of the metal had occurred. A cloudy appearance of the solution indicated the presence of a precipitate whereas clarity of the solution indicated a lack of precipitation. The results are shown in Table 2.

TABLE 2

| Metal | Concentration (mM) | Sulfate | Chloride | Nitrate |
|---|---|---|---|---|
| Cobalt | 300 | no ppt | no ppt | — |
|  | 150 | no ppt | no ppt | — |
| Nickel | 300 | no ppt | no ppt | — |
|  | 150 | no ppt | no ppt | — |
| Manganese | 300 | no ppt | ppt | — |
|  | 150 | no ppt | ppt | — |
| Cadmium | 300 | no ppt | ppt | — |
|  | 150 | no ppt | ppt | — |
| Zinc | 300 | ppt | ppt | — |
|  | 150 | ppt | ppt | — |
| Copper | 300 | no ppt | no ppt | no ppt |
|  | 150 | no ppt | no ppt | — | ppt: represents that the formation of a precipitate occurred after the addition of triethanolamine within a time course of 10 minutes
no ppt: represents that the formation of a precipitate did not occur after addition of triethanolamine to achieve a pH of 7.4 and within a time course of 10 minutes.
dashed line: not measured
Concentrations of the indicated metal are concentrations before addition of triethanolamine.

Example 4

Metal Loading is Distinct From Citrate-based Loading

The ability of doxorubicin to be accumulated in DPPC/DSPE-PEG2000 (95:5 mole ratio) liposomes according to the $MnSO_4$ and citrate based loading procedures was compared. Lipid films were hydrated with 300 mM $MnSO_4$ solution or 300 mM citrate, pH 3.5 and passed through an extrusion apparatus at 55° C. The resulting liposomes were run down a Sephadex G-50 column equilibrated with a buffering solution of SHE, pH 7.5 for $MnSO_4$ containing liposomes and HBS, pH 7.5 for citrate-containing liposomes. After buffer exchange, liposomes were combined with doxorubicin to give a final drug:lipid weight ratio of about 0.1:1, 0.2:1 or 0.3:1. The resulting mixture was incubated at 37° C. for 80 minutes. The extent of drug loading was determined as described in the methods by measuring the absorbance at 480 nm to quantify drug; lipid levels were measured by liquid scintillation counting.

Figure 7:
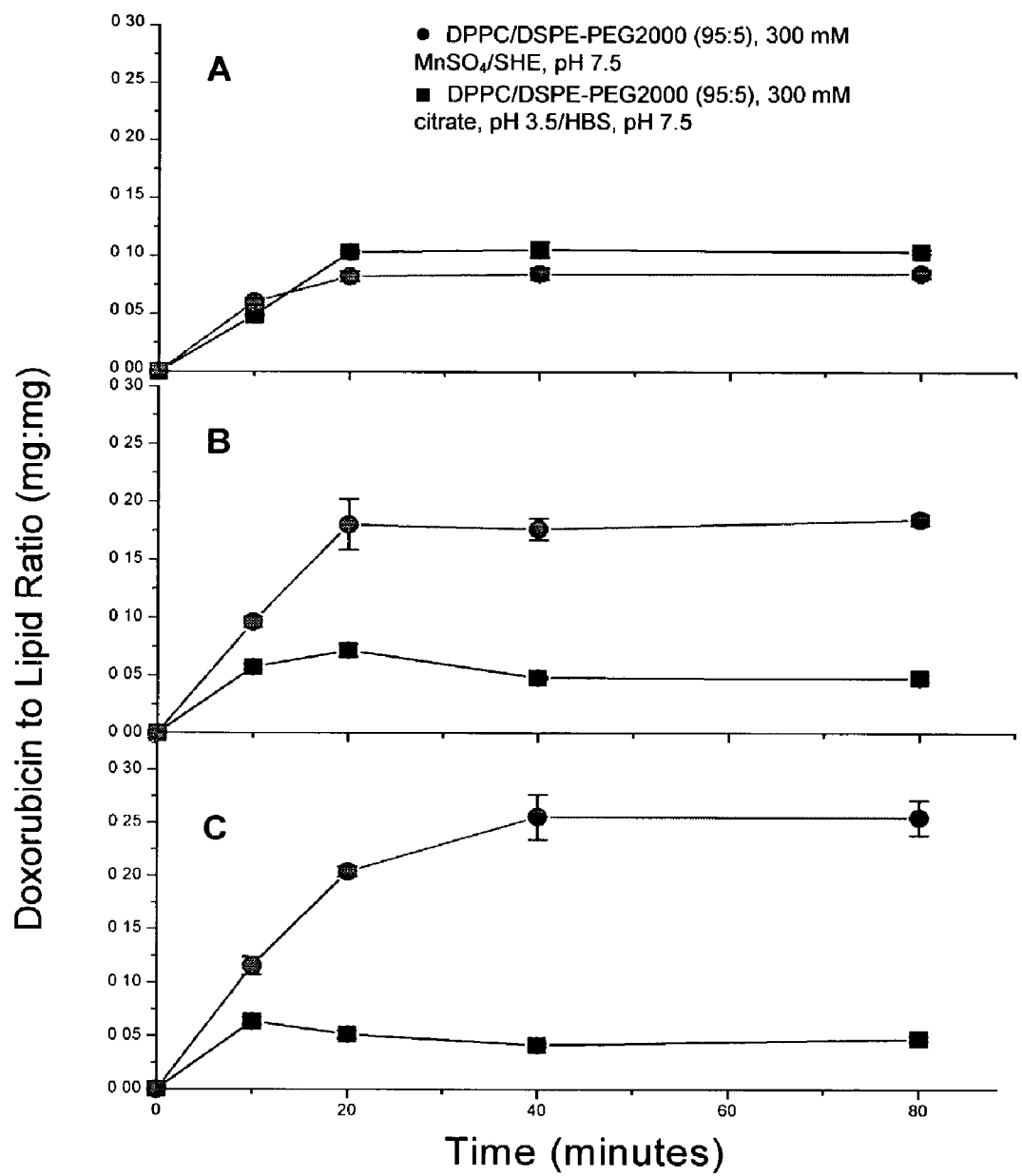
FIG. 7: A graph showing loading of doxorubicin into DPPC/DSPE-PEG2000 (95:5 mole ratio) liposomes as a function of time utilizing 300 mM $MnSO_4$ (●) or 300 mM citrate, pH 3.5 (■) as the internal medium. Doxorubicin loading was carried out at drug-to-lipid weight ratios of 0.1:1 (Panel A), 0.2:1 (Panel B) or 0.3:1 (Panel C) at 37° C. Data points represent the mean of three replicate experiments and the error bars represent the standard deviation.

Results summarized in FIG. 7 show that doxorubicin loading efficiencies of >95%, >90% and >80% were achieved in cholesterol-free liposomes containing $MnSO_4$ (300 mM) when the initial drug/lipid weight ratios were 0.1:1 (panel A), 0.2:1 (panel B) and 0.3:1 (panel C), respectively. In contrast, cholesterol-free liposomes loaded with doxorubicin according to the pH gradient citrate (300 mM citrate, pH 4.0), loading procedure under the same conditions displayed a substantial reduction in encapsulation efficiency as the doxorubicin/lipid weight ratio was increased from 0.1 to 0.3. The latter method could achieve a maximum drug-to-lipid weight ratio of <0.075. These results demonstrate that cholesterol-free liposomes can be efficiently loaded with doxorubicin to drug-to-lipid ratios as high as 0.3:1 (w/w) using metal loading whereas citrate-based loading procedures can only achieve a maximum drug-to-lipid ratios of 0.1:1 (w/w). These data show that metal-based loading mechanisms are distinct from those relying on maintaining a stable pH gradient. Data points represent the mean drug-to-lipid ratio and the error bars represent the standard deviation.

Example 5

Unbuffered Metal Loading Causes Collapse of the Transmembrane pH Gradient

The effect of doxorubicin loading on the transmembrane pH gradient of DMPC/Chol liposomes was compared using citrate and manganese loading techniques by measuring pH gradients prior to and subsequent to loading of drug. DMPC/Chol (55:45 mole ratio) lipid films were hydrated with 300 mM citrate buffer, pH 3.5, 300 mM $MnSO_4$ or 300 mM $MnCl_2$. The resulting MLVs were subjected to 5 freeze-and thaw cycles (freezing in liquid nitrogen and thawing at 40° C.) followed by extrusion at 40° C. To exchange the external solutions of the liposomes, samples were fractionated on Sephadex G-50 columns. For liposomes with encapsulated citrate, the external buffer was exchanged to HBS and for liposomes with encapsulated $MnSO_4$ and $MnCl_2$, the external buffer was exchanged to SHE, pH 7.5. Following buffer exchange, doxorubicin was added at a 0.2:1 weight ratio at 60° C. Absorbance at 480 nm following detergent solubilization was assessed to quantify drug and lipid levels were determined by liquid scintillation counting.

Figure 8:
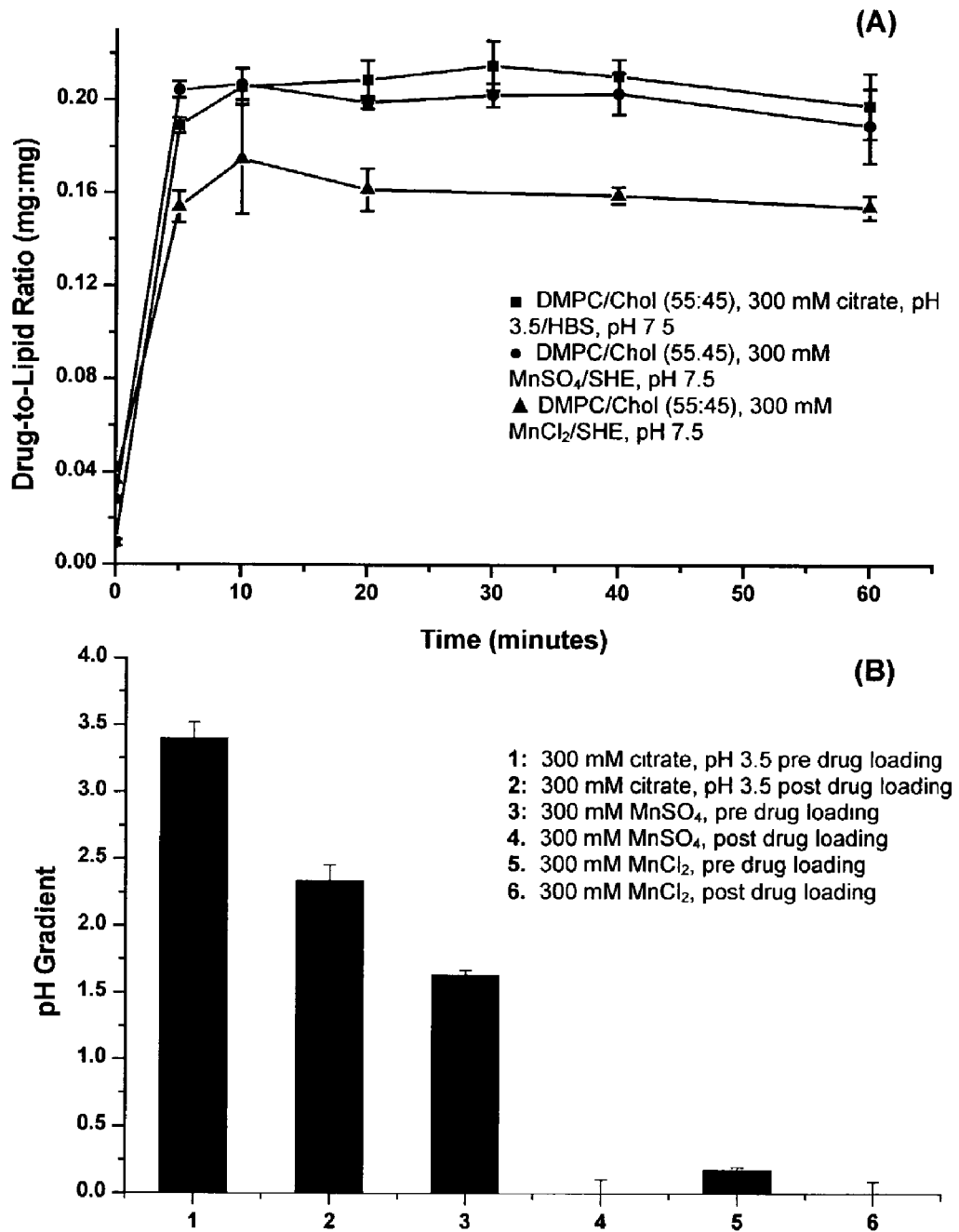
FIG. 8A: A graph showing loading of doxorubicin into DMPC/Chol (55:45 mole ratio) liposomes as a function of time using 300 mM $MnSO_4$ (●), 300 mM citrate, pH 3.5 (■) or 300 mM $MnCl_2$ (▲). Doxorubicin was loaded at a drug-to-lipid weight ratio of 0.2:1 at 60° C. Data points represent the mean of three replicate experiments and the error bars represent the standard deviation.
FIG. 8B: A histogram showing measured transmembrane pH gradients prior to and following doxorubicin loading under various conditions. The samples include those based on the citrate loading method prior to (column 1), and after doxorubicin loading (column 2); the $MnSO_4$ loading method prior to (column 3), and after doxorubicin loading (column 4); and the $MnCl_2$ loading method prior to (column 5) and after doxorubicin loading (column 6). The results represent the mean pH gradient of three separate experiments and the error bars indicate the standard deviation.

Results presented in FIG. 8A show that loading of doxorubicin into liposomes containing encapsulated citrate (squares) and $MnSO_4$ (circles) was essentially complete within 5 minutes of incubation. Doxorubicin accumulation employing $MnCl_2$ (triangles) was less complete in relation to $MnSO_4$ and citrate loading. Data points represent the mean drug-to-lipid ratios of at least three replicate experiments and the error bars indicate the standard deviation.

Transmembrane pH gradients of the formulations before and after doxorubicin loading were measured using [14C]-methylamine. Briefly, [14C]-methylamine (0.5 (Ci/mL) was added to the liposome solutions prepared above. After 15 minutes, 150 (L aliquots were passed down 1 mL Sephadex G-50 columns equilibrated in HBS to remove unencapsulated methylamine. Lipid and methylamine concentrations before and after column chromatography were determined by scintillation counting. The transmembrane pH gradient was calculated according to the relationship:

$$pH=\log\{[H+]\text{inside}/[H+]\text{outside}=\log\{[\text{methylamine}]\text{inside}/[\text{methylamine}]\text{outside}\}.$$

As shown in FIG. 8B, following the establishment of the pH gradient, but prior to doxorubicin loading, the formulations with encapsulated citrate (column 1), $MnSO_4$ (column 3), $MnCl_2$ (column 5) exhibited measured pH gradients of 3.4, 1.6 and less than 0.18, respectively. These results indicate that transmembrane pH gradients are smaller when manganese solutions are utilized in relation to citrate. Following addition of doxorubicin to liposomes containing encapsulated citrate, the pH gradient decreased from 3.4 (column 1) to 2.3 (column 2). This result is consistent with previous reports demonstrating doxorubicin-mediated collapse of the pH gradient in these formulations. Following doxorubicin loading, the manganese-containing liposomes exhibited no measurable pH gradient (columns 4 and 6) thus demonstrating that these formulations lose their pH gradient during loading of drug. Data points represent the mean pH gradient of three separate experiments and the errors bars indicate the standard deviation.

Example 6

Loading Efficiency is Dependent on the Metal Ion Employed

Loading of irinotecan into DSPC/DSPE-PEG2000 (95:5 mole ratio) liposomes encapsulating manganese sulfate or copper sulfate solutions was carried out in order to compare the loading efficiency of the two different metals.

Lipid films were hydrated in a solution of either 300 mM $MnSO_4$ or 300 mM $CuSO_4$. The resulting multilamellar vesicles (MLVs) were extruded at 60° C. and the LUVs were buffer exchanged into SHE, pH 7.4. Drug loading was initiated by the addition of irinotecan to the resulting solution at a 0.1:1 drug-to-lipid weight ratio at 60° C. The extent of drug loading was measured as described and absorbance was measured at 370 nm.

Figure 9:
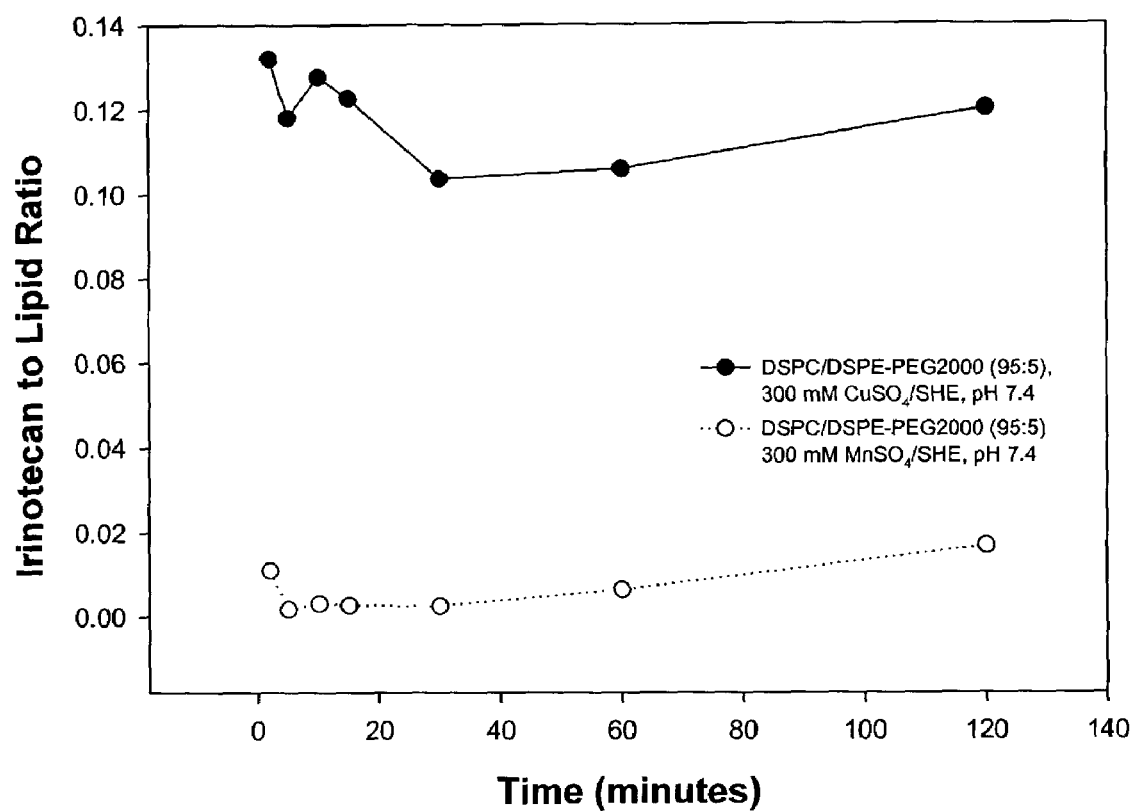
FIG. 9: A graph showing loading of irinotecan into DSPC/DSPE-PEG2000 (95:5 mole ratio) liposomes utilizing either 300 mM $MnSO_4$ (○) or 300 mM $CUSO_4$ (●) as the internal loading medium. Irinotecan was loaded at 60° C. at a drug-to-lipid weight ratio of 0.1:1.

Results in FIG. 9 demonstrate that manganese loading of irinotecan was only 10% complete at the 30-minute time point, whereas irinotecan loading into copper containing liposomes resulted in greater than 95% loading within 5 minutes. These results illustrate that the loading properties of liposomes are highly dependent on the identity of the metal ion.

Example 7

Loading of Drug into Cholesterol-free Liposomes Using Encapsulated Manganese, Cobalt and Nickel Uptake of daunorubicin into cholesterol-free liposomes (DSPC/DSPE-PEG2000) was investigated using internal $MnSO_4$, $CoCl_2$ and $NiSO_4$ solutions at various loading temperatures.

Cholesterol-free (DSPC/DSPE-PEG2000, 95:5 mole ratio) liposomes encapsulating manganese were prepared by hydration of lipid films in 300 mM $MnSO_4$ and extrusion was carried out at 75° C. The samples were exchanged into HBS using a hand held tangential flow dialysis column. The external buffer contained 1.67 mM EDTA to remove any divalent cations. Daunorubicin was loaded at a drug-to-lipid weight ratio of 0.1:1 and loading was carried out at 23° C., 37° C. or 60° C. The extent of drug loading was measured by solubilizing the liposomes in detergent followed by measuring the absorbance at 480 nm.

Figure 10A:
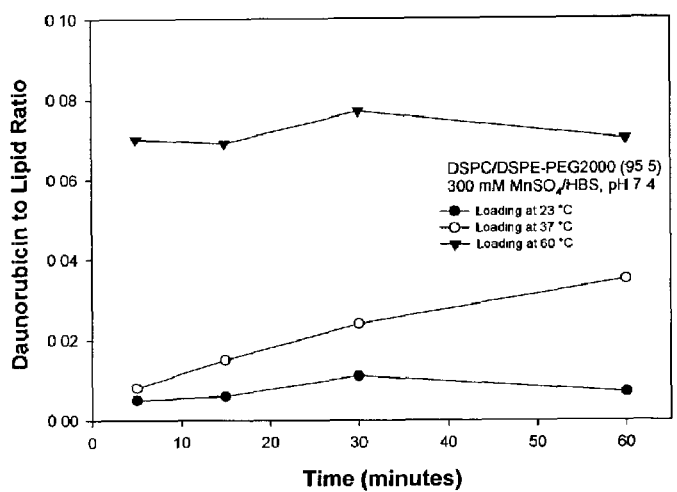
FIG. 10A: A graph showing loading of daunorubicin into DSPC/DSPE-PEG2000 (95:5 mole ratio) liposomes as a function of time using 300 mM $MnSO_4$ as the internal medium. Loading was carried out at 23° C. (●), 37° C. (○) and 60° C. (▼) at an initial drug-to-lipid weight ratio of 0.1:1.

Results in FIG. 10A show that loading of daunorubicin into DSPC/DSPE-PEG2000 (95:5 mole ratio) $MnSO_4$ containing liposomes is most efficient at 60° C. whereas loading at 23° C. and 37° C. occurred to a lesser extent. Daunorubicin to lipid ratios (mol:mol) of 0.07 can be achieved when the loading temperature is at 60° C.

Cobalt containing DSPC/DSPE-PEG2000 (95:5 mole ratio) liposomes were prepared by hydration of lipid films in 150 mM $CoCl_2$. MLVs were extruded at 75° C. and the exterior buffer was then exchanged by dialyzing against HBS overnight. The liposomes were then further exchanged into HBS using a hand held tangential flow dialysis column to remove any residual $CoCl_2$. Daunorubicin was loaded at 23, 37 and 60° C. at a drug/lipid weight ratio of 0.1:1. The extent of daunorubicin loading was determined by measuring the absorbance at 480 nm after solubilization of the liposomes. Lipid levels were determined by liquid scintillation counting.

Figure 10B:
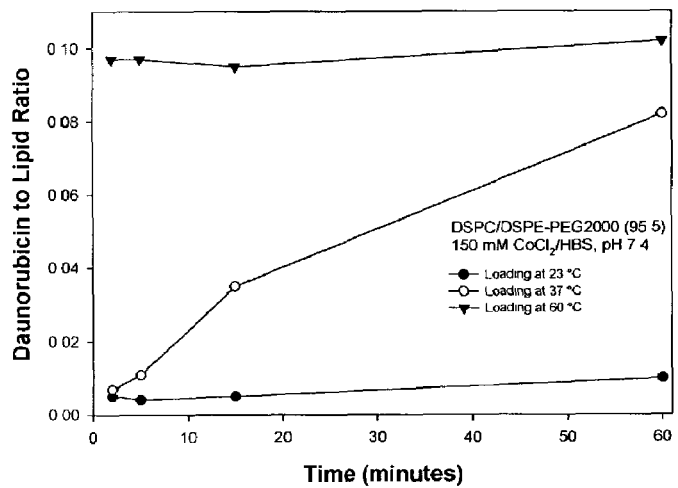
FIG. 10B: A graph showing loading of daunorubicin into DSPC/DSPE-PEG2000 (95:5 mole ratio) liposomes as a function of time using 150 mM CoCl2, as the internal medium. Loading was carried out at 23° C. (●), 37° C. (○) and 60° C. (▼) at a drug-to-lipid weight ratio of 0.1:1.

Daunorubicin was efficiently loaded into $CoCl_2$ containing DSPC/DSPE-PEG2000 (95:5 mole ratio) liposomes at 60° C. (see FIG. 10B). At 60° C., loading resulted in >95% encapsulation of daunorubicin within 5 minutes. Loading at 23° C. and 37° C. was less efficient and a 60 minute incubation at 37° C. was required to achieve 80% drug encapsulation.

Liposomes containing DSPC/DSPE-PEG2000 (95:5 mole ratio) and encapsulating NiSO4 were prepared as described in the previous examples. Lipid films were hydrated in 300 mM NiSO4 and the external buffer of the liposomes was exchanged by passage through a Sephadex G-50 column equilibrated with SHE, pH 7.4. Daunorubicin was added such that the initial (prior to loading) drug-to-lipid weight ratio was 0.2 to 1 and loading was carried out at 60° C. Loading efficiencies of daunorubicin were measured as described above by UV absorption.

Figure 10C:
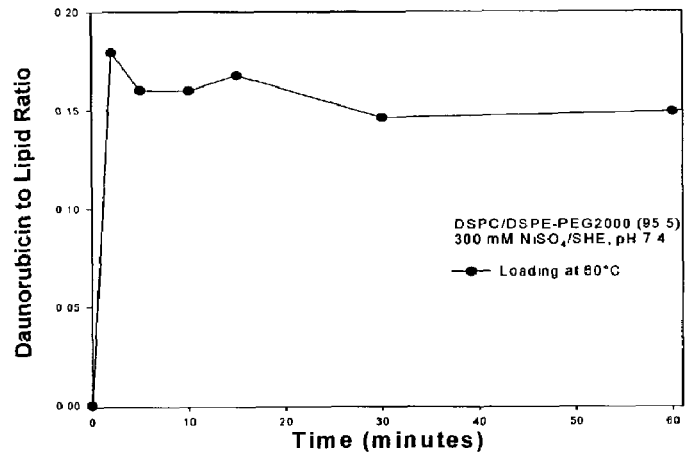
FIG. 10C: A graph showing loading of daunorubicin into DSPC/DSPE-PEG2000 (95:5 mole ratio) liposomes as a function of time using 300 mM $NiSO_4$ as the internal medium. Loading was carried out at 60° C. at a drug-to-lipid weight ratio of 0.2:1.

Results in FIG. 10C demonstrate that incubation of daunorubicin with NiSO4 containing DSPC/DSPE-PEG2000 liposomes at 60° C. resulted in greater than 75% drug encapsulation within 5 minutes.

Example 8

Loading of Drug into Cholesterol-free Liposomes Employing Encapsulated Copper

Copper loading of epirubicin into DSPC/DSPE-PEG2000 (95:5 mole ratio) liposomes was also examined.

Copper containing DSPC/DSPE-PEG2000 (95:5 mole ratio) liposomes were prepared as described in the previous examples. Lipid films were hydrated in 300 mM $CuSO_4$ and extrusion was carried out at 70° C. The external buffer was replaced with SHE, pH 7.4 by passing liposomes through a Sephadex G-50 column equilibrated with SHE buffer prior to loading. Epirubicin was added to the copper-containing liposomes at a drug-to-lipid weight ratio of about 0.2:1 and loading was carried out at 60° C. Epirubicin and lipid levels were assayed by spectrophotometry and scintillation counting respectively. To quantify epirubicin, the absorbance was measured at 480 mn after solubilizing the liposome preparation with detergent.

Figure 11:
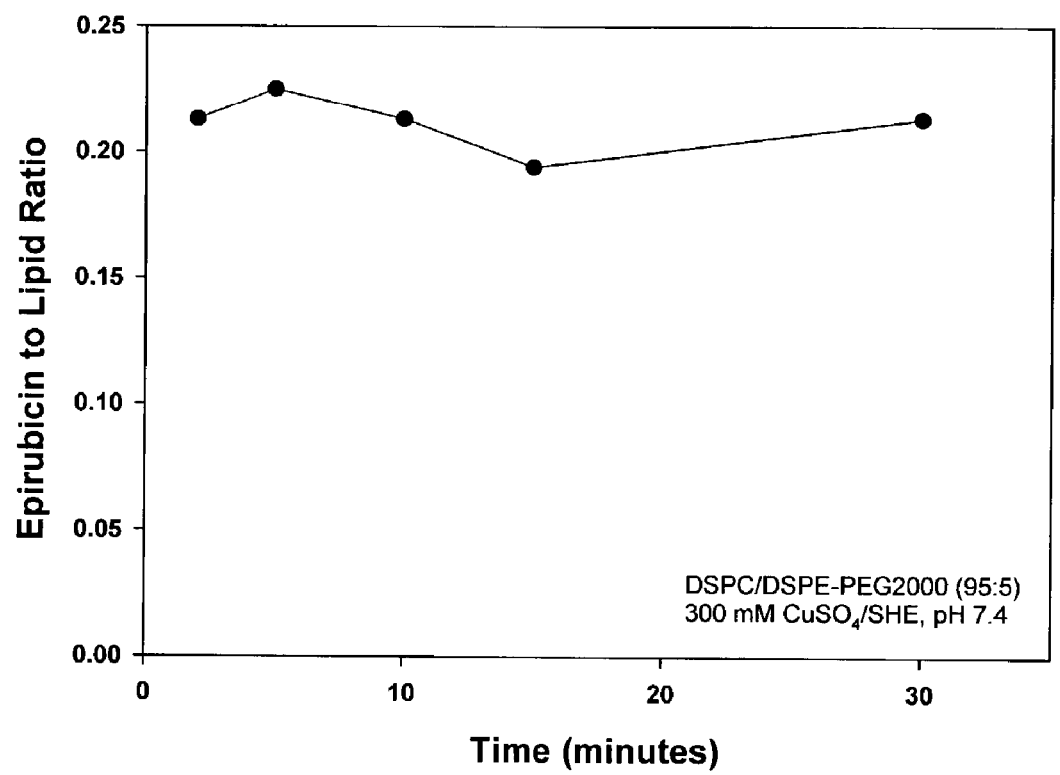
FIG. 11: A graph showing loading of epirubicin into DSPC/DSPE-PEG2000 (95:5 mole ratio) liposomes as a function of time using 300 mM $CUSO_4$ at 60° C. Epirubicin was loaded to achieve a drug-to-lipid weight ratio of 0.2:1.

FIG. 11 shows that loading of epirubicin into DSPC/DSPE-PEG2000 (95:5 mole ratio) liposomes resulted in >95% drug accumulation within 5 minutes when uptake occurred at 60° C.

Example 9

Metal Loading of Cholesterol-containing Liposomes

Uptake of doxorubicin, daunorubicin and topotecan into DSPC/Chol (55:45 mole ratio) liposomes was investigated using liposomes prepared to encapsulate copper and cobalt.

DSPC/Chol (55:45 mole ratio) liposomes encapsulating cobalt were prepared as described above by hydration of lipid films in a solution of 300 mM $CoCl_2$. The external buffer was exchanged by column chromatography to SHE, pH 7.5. Loading was initiated by the addition of doxorubicin at a drug-to-lipid weight ratio of approximately 0.1:1. Liposomes were then incubated at 60° C. to facilitate drug loading. The extent of drug loading was measured as described previously by solubilization of the samples with detergent followed by measurement of the absorbance at 480 nm.

Figure 12A:
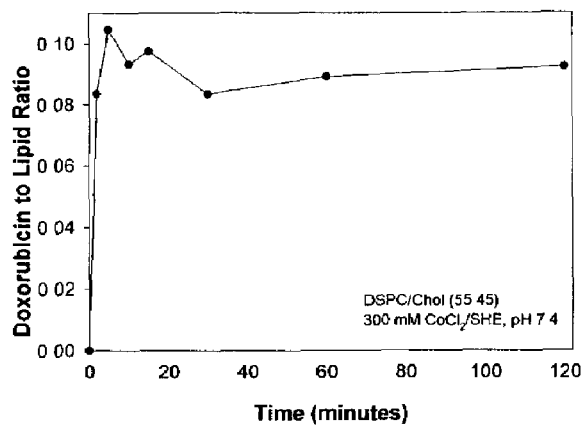
FIG. 12A: A graph showing loading of doxorubicin into DSPC/Chol (55:45 mole ratio) liposomes as a function of time using 300 mM CoCl2 as the internal medium and SHE, pH 7.5 as the external buffer. Loading was carried out at 60° C. at a drug-to-lipid weight ratio of 0.1:1.

Results in FIG. 12A show that within 10 minutes, >90% of the added drug was encapsulated.

Copper sulfate containing DSPC/Chol (55:45 mole ratio) liposomes were prepared by hydration of a lipid film in 300 mM $CuSO_4$. The resulting MLVs were extruded at 70° C. and the external solution was exchanged to HBS by passage through a Sephadex G-50 spin column. The buffer exchanged liposomes were loaded at 60° C. with daunorubicin at a 0.1:1, 0.2:1 or 0.4:1 drug-to-lipid weight ratio. Liposomes were solubilized in detergent prior to determining drug levels by measuring the absorbance at 480 nm.

Figure 12B:
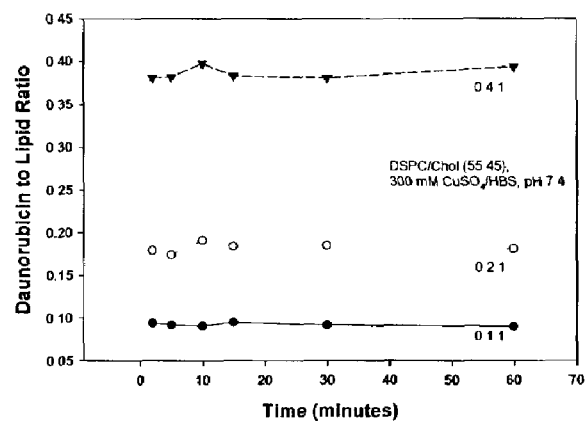
FIG. 12B: A graph showing loading of daunorubicin into DSPC/Chol (55:45 mole ratio) liposomes as a function of time using 300 mM $CuSO_4$ as the internal medium and HBS, pH 7.4 as the external buffer. Daunorubicin was loaded at 60° C. at a drug-to-lipid weight ratio of 0.1:1 (●), 0.2:1 (○) and 0.4:1 (▼).

Results in FIG. 12B indicate that drug loading into DSPC/Chol (55:45 mole ratio) liposomes loaded using encapsulated $CuSO_4$ was efficient with >90% of the added drugs encapsulated within 5 minutes at 60° C.

DSPC/Chol (55:45 mole ratio) liposomes encapsulating 300 mM $CuSO_4$ were prepared as described for FIG. 12B except that the external buffer was exchanged to SHE, pH 7.4. The liposomes were then incubated with topotecan at a 0.1:1 drug/lipid weight ratio at 37° C. The extent of loading was monitored for 2 hours at the indicated time points by quantifying drug absorbance at 380 nm and lipid by liquid scintillation counting. Drug was quantified by measuring absorbance at 380 nm.

Figure 12C:
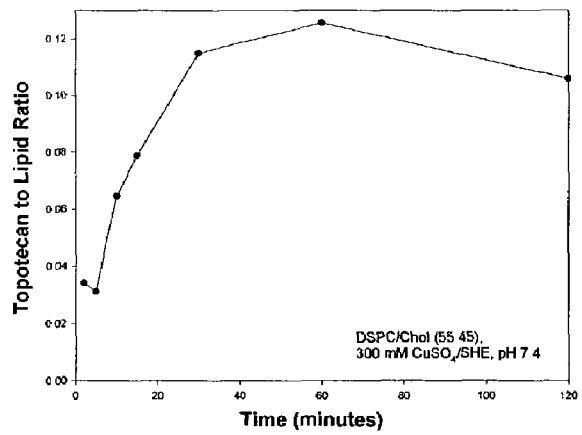
FIG. 12C: A graph showing loading of topotecan into DSPC/DSPE-PEG (95:5 mole ratio) liposomes as a function of time at 37° C. A 300 mM $CuSO_4$ solution was used as the internal loading medium. Topotecan was loaded at a drug-to-lipid weight ratio of 0.1:1.

FIG. 12C indicates that the loading of topotecan into DSPC/Chol (55:45 mole ratio) liposomes was essentially 100% (>95%) complete within 30 minutes.

Example 10

Metal Loading of a Number of Different Drugs into Unbuffered Liposomes Containing Passively Encapsulated Drug Loading of daunorubicin or irinotecan into various liposomes containing a passively encapsulated drug was investigated under a number of conditions.

Daunorubicin uptake into cisplatin-containing liposomes was measured according to the following procedures. DSPC/DSPE-PEG2000 (95:5 mole ratio) or DMPC/Chol (55:45 mole ratio) liposomes were prepared according to the materials and methods of the preceding examples. The lipid films were hydrated in 150 mM $MnCl_2$ or 150 mM $CuCl_2$, respectively, with 8.5 mg/mL cisplatin at 80° C. The MLVs were extruded at 75° C. Precipitated cisplatin was removed by centrifugation and the samples were then dialyzed against HBS overnight. Samples containing $CuCl_2$ were further exchanged into HBS using a hand held tangential flow dialysis column to remove any residual $CuCl_2$ or cisplatin. Daunorubicin was loaded into cisplatin/$MnCl_2$ and cisplatin/$CuCl_2$ containing liposomes at a drug/lipid weight ratio of 0.1:1 at an incubation temperature of 60° C. The initial cisplatin drug/lipid weight ratio was 0.01:1 for both liposome compositions. The extent of drug loading was measured as described previously by solubilization of the samples with detergent followed by measurement of the absorbance at 480 nm.

Figure 13A:
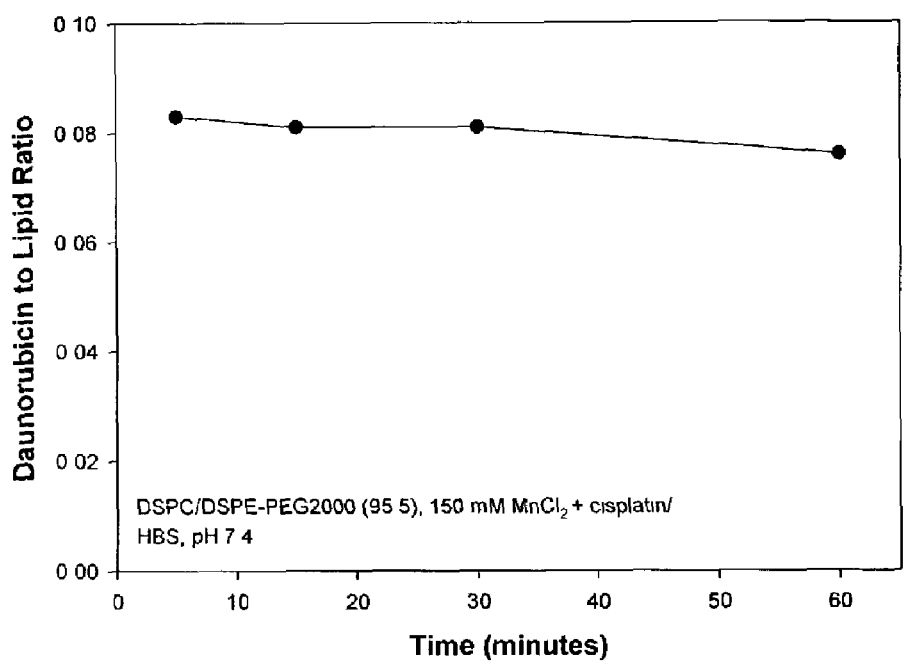
FIG. 13A: A graph showing loading of daunorubicin into cisplatin-containing DSPC/DSPE-PEG2000 (95:5 mole ratio) liposomes as a function of time using 150 mM $MnCl_2$ as the internal medium and HBS, pH 7.4 as the external solution. Cisplatin was passively encapsulated and daunorubicin loading was carried out at 60° C. at a drug-to-lipid weight ratio of 0.1:1.
Figure 13B:
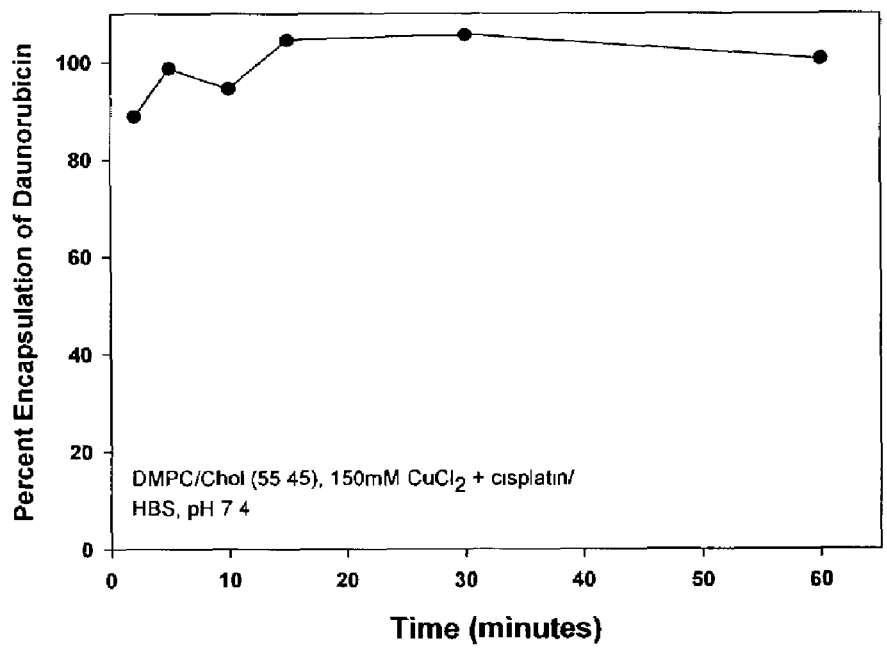
FIG. 13B: A graph showing loading of daunorubicin into cisplatin-containing DMPC/Chol (55:45 mole ratio) liposomes as a function of time using 150 mM $CuCl_2$ as the internal medium and HBS, pH 7.4 as the external solution. Cisplatin was passively encapsulated and daunorubicin loading was carried out at 60° C. at a drug-to-lipid weight ratio of 0.1:1.

FIGS. 13A and 13B show that DSPC/DSPE-PEG2000 (95:5 mole ratio) and DMPC/Chol (55:45 mole ratio) liposomes preloaded with cisplatin can be loaded with a second drug (daunorubicin) when using either manganese- or copper-based active loading, respectively. Furthermore, daunorubicin encapsulation was not as efficient using $MnCl_2$ compared to $CuCl_2$.

Loading of daunorubicin or irinotecan into DPPC/Chol (55:45 mole ratio) liposomes containing either passively entrapped carboplatin or cisplatin, respectively, was analyzed using nickel or copper loading. Lipid films were hydrated in 300 mM $NiSO_4$ or 75 mM $CuCl_2$+150 mM $CuSO_4$ with 40 mg/ml carboplatin or 8.5 mg/mL cisplatin, respectively. MLVs were extruded at 70° C. Nickel-containing samples were dialyzed overnight against 1 L 300 mM sucrose, 20 mM HEPES, pH 7.4, while samples containing copper were exchanged into SHE, pH 7.4, by chromatography on Sepharose columns containing CL4B resin. Daunorubicin was loaded at 37° C. at a drug-to-lipid weight ratio of 0.1:1. Irinotecan was loaded into liposomes as previously described at 60° C. at a drug-to-lipid weight ratio of 0.1. Drug and lipid levels were measured using procedures previously described.

Figure 13C:
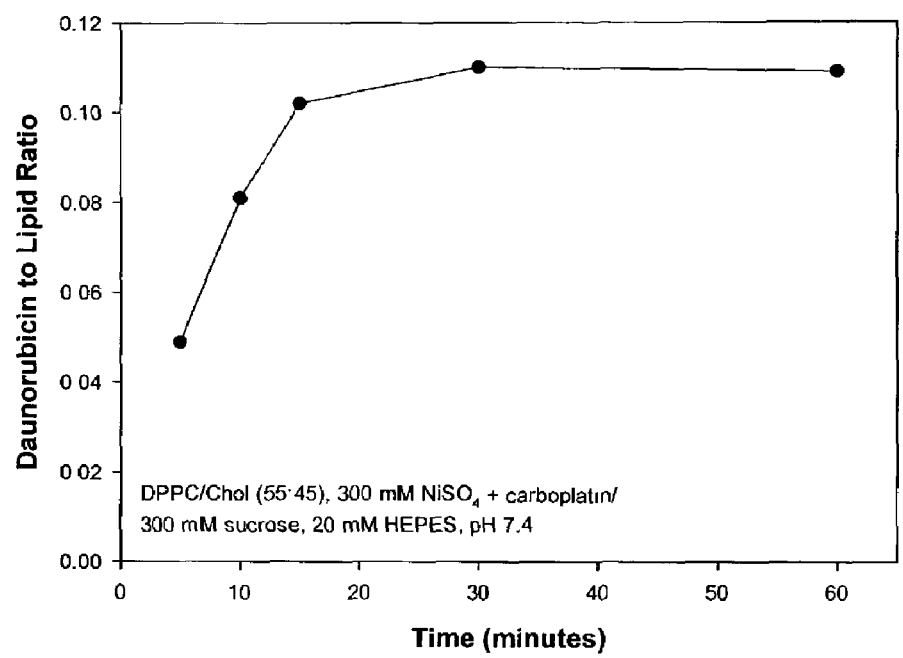
FIG. 13C: A graph showing loading of daunorubicin into carboplatin-containing DPPC/Chol (55:45 mole ratio) liposomes as a function of time using 300 mM $NiSO_4$ as the internal medium and 300 mM sucrose, 20 mM HEPES, pH 7.4 as the external solution. Carboplatin was passively encapsulated and daunorubicin loading was carried out at 37° C. at a drug-to-lipid weight ratio of 0.1:1.
Figure 13D:
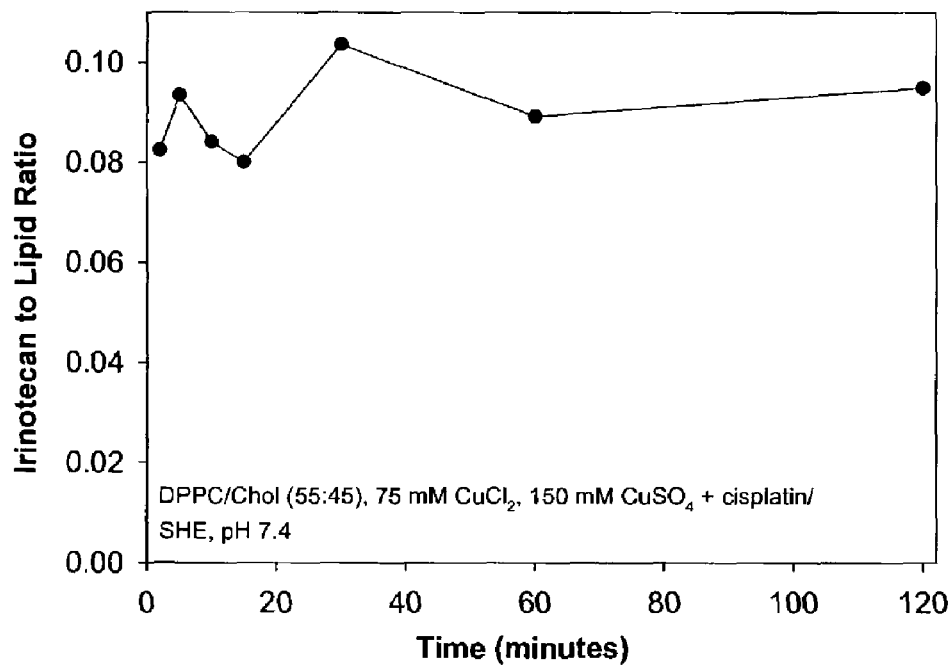
FIG. 13D: A graph showing loading of irinotecan into cisplatin-containing DPPC/Chol (55:45 mole ratio) liposomes as a function of time using 75 mM $CuCl_2$+150 mM $CuSO_4$ as the internal medium and SHE, pH 7.4 as the external solution. Cisplatin was passively encapsulated and irinotecan loading was carried out at 60° C. at a drug-to-lipid weight ratio of 0.1:1.

Results summarized in FIGS. 13C and 13D illustrate that DPPC/Chol (55:45 mole ratio) liposomes prepared with either nickel or copper ion solutions containing a platinum drug, efficiently load a second drug.

Example 11

Metal Loading Combined with Ionophore-mediated Loading Techniques Results in Encapsulation of Multiple Agents Combining metal loading with an additional active loading mechanism results in efficient encapsulation of both doxorubicin and vincristine into a single liposome. Metal loading of doxorubicin followed by ionophore-mediated loading of vincristine is detailed below.

DSPC/cholesterol liposomes (55:45 mole ratio) were prepared as described in the preceding examples except that lipid films were hydrated in 300 mM $MnSO_4$ and the lipid marker 14C-CHE was used. The resulting MLVs were extruded at 65° C. and then passed through a Sephadex G-50 column that had been pre-equilibrated with 300 mM sucrose, 20 mM HEPES and 15 mM EDTA (pH 7.5). Doxorubicin was then added in a 0.2:1 drug-to-lipid weight ratio and further incubated at 60° C. for 60 minutes.

Following loading of doxorubicin, the divalent cation ionophore A23187 (1?g ionophore/(mol lipid) was added to the liposomes and the mixture was incubated at room temperature for 3 minutes to facilitate A23187 incorporation into the bilayer. Subsequently, vincristine was added to the mixture and incubated at 50° C. for 100 minutes. A small amount of radiolabeled vincristine was added to the drug preparation to facilitate drug quantitation. Drug uptake was performed at a 0.05:1 vincristine to lipid weight ratio. Vincristine and lipid was quantified by scintillation counting following liposome solubilization with detergent. Absorbance at 480 nm was used to quantify doxorubicin levels.

Figure 14:
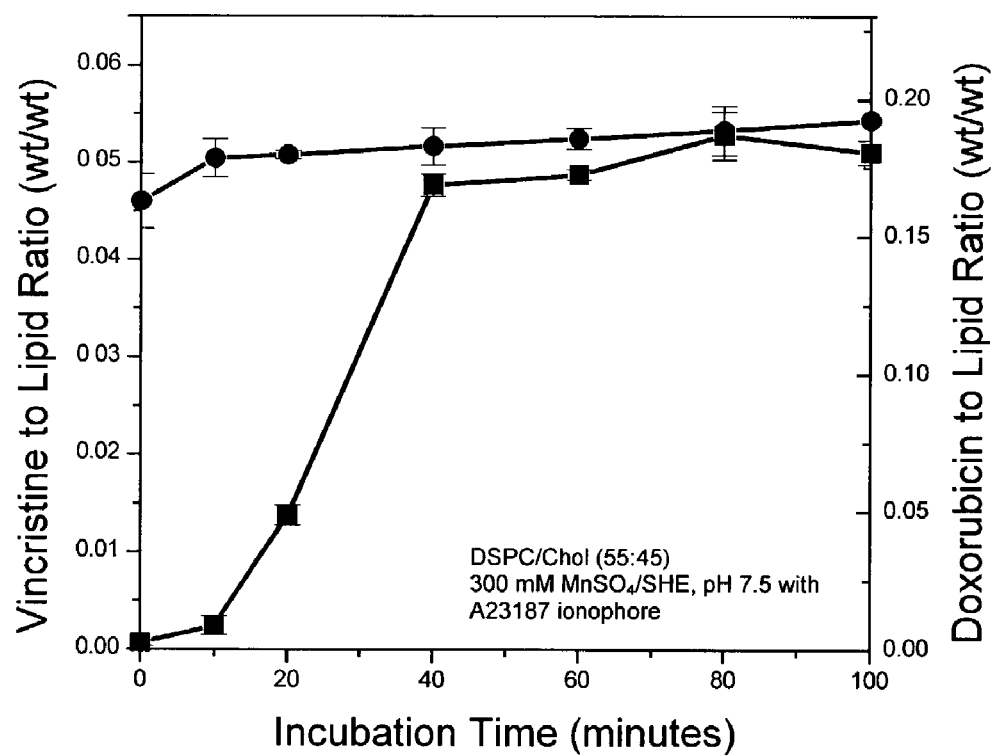
FIG. 14: A graph showing vincristine/lipid and doxorubicin/lipid ratios at various time points during loading of vincristine at 50° C. into DSPC/Chol (55:45 mole ratio) liposomes preloaded with doxorubicin. Liposomes containing 300 mM $MnSO_4$ were preloaded with doxorubicin (●) at 50° C. at a drug-to-lipid ratio of 0.2:1 wt/wt. Vincristine loading (■) was carried out with the aid of the A23187 ionophore at a drug-to-lipid ratio of 0.05:1 wt/wt. Error bars represent the standard deviation between three replicate experiments.

FIG. 14 shows that liposomes preloaded with doxorubicin (circles) through metal loading display near maximum encapsulation of ionophore-mediated loading of vincristine (squares) after 40 minutes of incubation at 50° C., with no significant leakage of doxorubicin during vincristine encapsulation. The data points represent the mean drug-to-lipid ratio of three separate experiments and the error bars indicate the standard deviation.

Example 12

Metal Loading of Two Drugs in the Absence of Ionophore Results in Efficient Encapsulation of Two Drugs The preceding examples have made use of either passive or ionophore-mediated loading procedures in combination with active metal loading to result in encapsulation of two drugs into liposomes of various compositions. The following example demonstrates that metal loading alone can be utilized to actively load two drugs into a single liposome. Doxorubicin and irinotecan were loaded into DSPC/Cholesterol liposomes as described below.

DSPC/Chol liposomes (55:45 mole ratio) were prepared as detailed previously with encapsulated 300 mM $CuSO_4$. The extruded liposomes were passed through a Sephadex G-50 column that had been pre-equilibrated with SHE, pH 7.5. Irinotecan was loaded first at a drug-to-lipid mole ratio of 0.2:1 at 60° C. to approximately 100% encapsulation. Following this, doxorubicin was incubated at 60° C. at a drug-to-lipid mole ratio of 0.15:1 with the irinotecan-containing liposomal formulation to allow sufficient loading of doxorubicin. Irinotecan levels were measured by measuring the absorbance at 370 nm using a standard curve prepared in the presence of doxorubicin to account for its absorbance at 370 nm. Similarly, doxorubicin concentrations were determined by measuring absorbance at 480 nm using a standard curve prepared in the presence of irinotecan to account for its absorbance at 480 run. As a control, individual uptake of each drug was measured separately into liposomes of the same composition.

Figure 15:
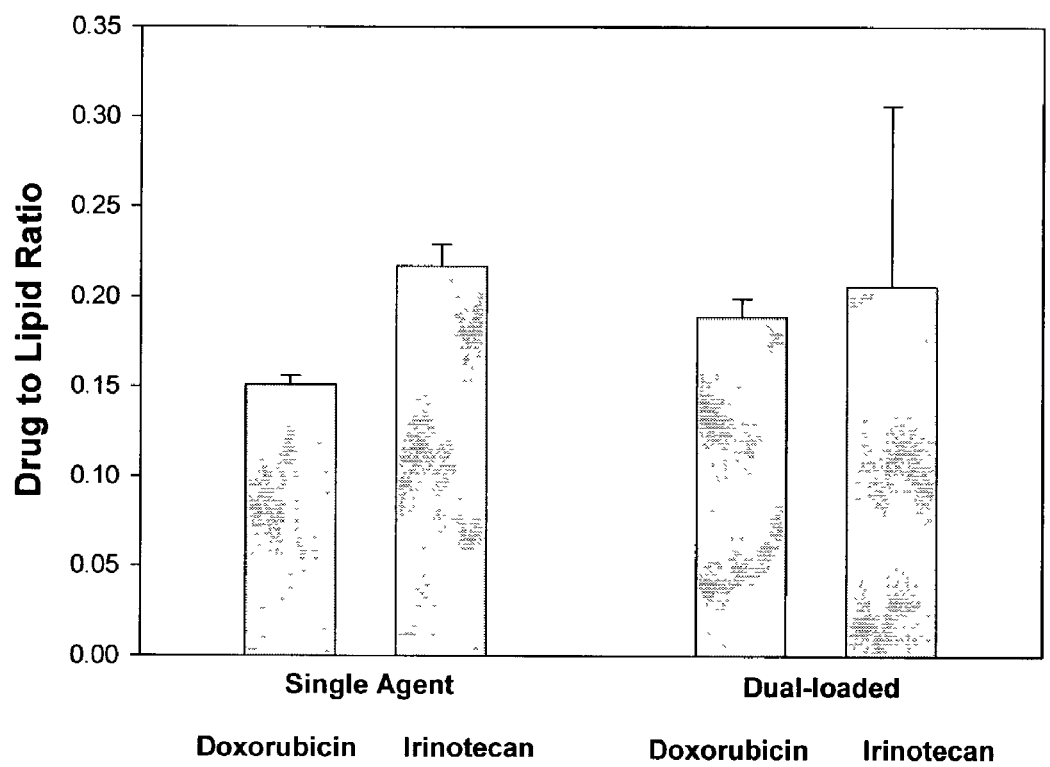
FIG. 15: A histogram showing sequential metal loading of irinotecan and doxorubicin into DSPC/Chol (55:45 mole ratio) liposomes containing 300 mM $CuSO_4$ as the internal medium. Liposomes were preloaded with irinotecan at 60° C. at a drug-to-lipid mole ratio of 0.2:1 to approximately 100% followed by encapsulation of doxorubicin, loaded at a 0.15:1 drug/lipid mole ratio. As a control, liposomal uptake of each drug into singly loaded liposomes was measured separately. Error bars represent the standard deviation between three replicate experiments.

The results summarized in FIG. 15 illustrate that doxorubicin and irinotecan can be efficiently loaded into a single liposome using the active metal loading procedure of the invention. The results represent the mean drug-to-lipid ratio of three separate experiments and the error bars indicate the standard deviation.

Example 13

Drug Release Rates in vivo are Dependent on the Nature of the Metal Ion

The ability of different internal loading mediums to control the release of daunorubicin from DSPC/DSPE-PEG2000 (95:5 mole ratio) liposomes in vivo, was investigated using 150 mM citrate, pH 4.0, 300 mM $CuSO_4$ and 300 mM $MnSO_4$. DSPC/DSPE-PEG2000 liposomes were prepared as described and extruded at 75° C. The external solution was exchanged to HBS by dialysis against HBS. Daunorubicin was loaded at a drug-to-lipid weight ratio of about 0.1:1 and loading was carried out at 60° C. Daunorubicin loading was measured as described in the preceding examples using EDTA in the solubilization buffer. The drug-loaded liposomes were then intravenously administered to Balb/c mice at lipid doses of 100 mg/kg and daunorubicin doses of 10 mg/kg. Blood was recovered 24 hours after administration by cardiac puncture (3 mice per time point) and collected into EDTA-containing tubes. Plasma lipid concentrations were determined by liquid scintillation counting. Daunorubicin was extracted from plasma as follows:

A defined volume of plasma was adjusted to 200 (L with distilled water followed by addition of 600 (L of distilled water, 100 (L of 10% SDS and 100 (L of 10 mM $H_2SO_4$. The resulting mixture was mixed and 2 mL of 1:1 isopropanol/chloroform was added followed by vortexing. The samples were frozen at −20° C. overnight or −80° C. for 1 hour to promote protein aggregation, brought to room temperature, vortexed and centrifuged at 3000 rpm for 10 minutes. The bottom organic layer was removed and assayed for fluorescence intensity at 500 nm as the excitation wavelength (2.5 nm bandpass) and 550 nm as an emission wavelength (10 nm bandpass) and using an absorbance wavelength of 480 nm.

Figure 16:
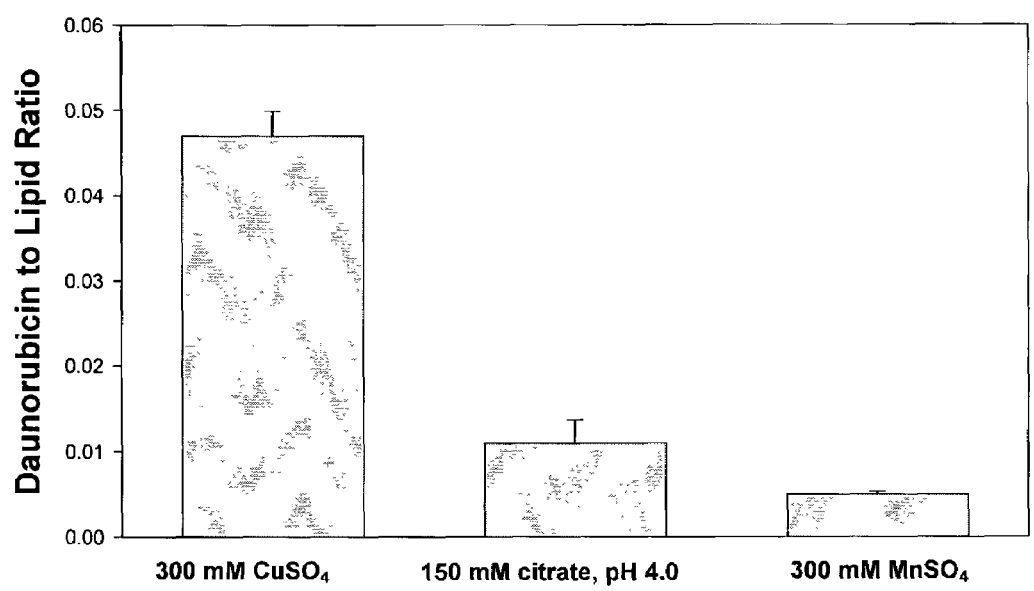
FIG. 16: A histogram showing the plasma drug-to-lipid ratio of daunorubicin-containing DSPC/DSPE-PEG2000 (95:5 mole ratio) liposomes 24 hours after intravenous administration to Balb/c mice. Daunorubicin was loaded at a drug-to-lipid weight ratio of 0.1:1 at 60° C. into liposomes comprising either 300 mM $CuSO_4$; 150 mM citrate, pH 4; or 300 mM $MnSO_4$ as the internal medium. Error bars represent the standard deviation between three replicate experiments.

FIG. 16 demonstrates that DSPC/DSPE-PEG2000 (95:5 mole ratio) liposomes loaded with daunorubicin employing encapsulated citrate, pH 4.0, $CuSO_4$ and $MnSO_4$ display differing plasma drug-to-lipid ratios 24 hours after intravenous administration. These results thus show that drug release can be controlled through selection of an appropriate metal ion. The results represent the mean drug-to-lipid ratio of at least three separate experiments and the error bars indicate the standard deviation.

Example 14

Loading Liposomes in the Presence and Absence of Uncomplexed Metal Ions

Figure 17:
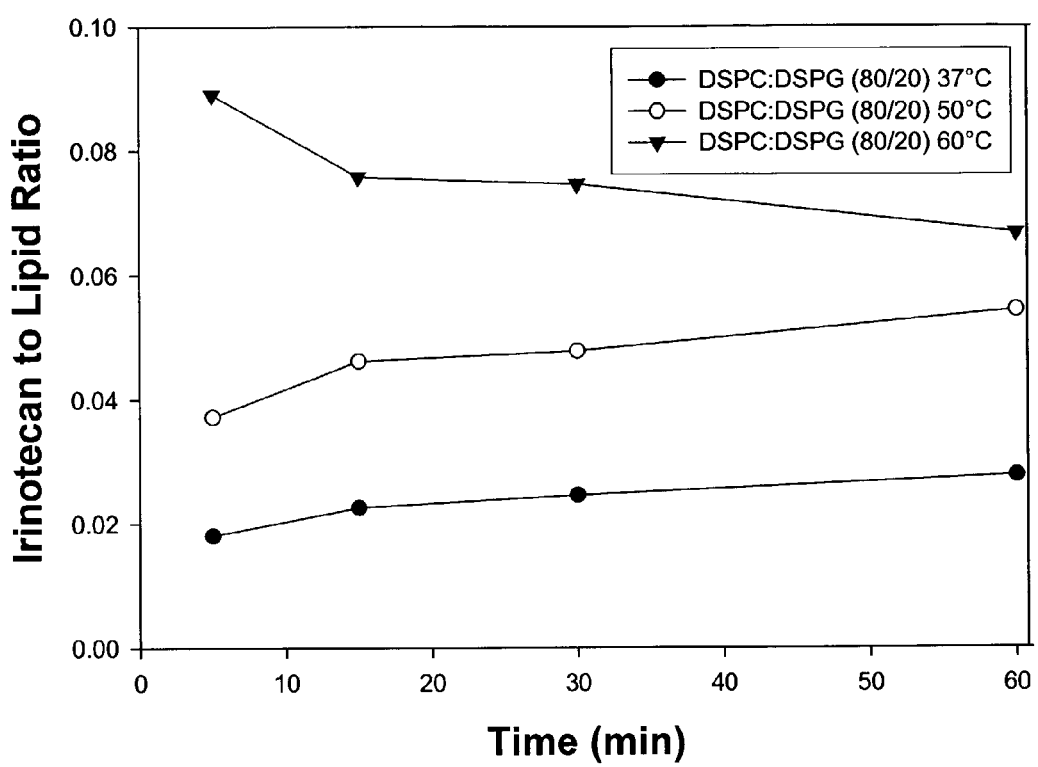
FIG. 17: a graph showing loading of irinotecan into DSPC/DSPG (80:20 mol ratio) liposomes in response to encapsulated $CUSO_4$ following passage of the liposomes through a Chelex-100™ column equilibrated with 150 mM NaCl. The liposomes were subsequently exchanged into 300 mM sucrose, 20 mM HEPES, pH 7.4. Loading was carried out by incubation at 37° C. (●), 50° C. (○) and 60° C. (▼).
Figure 18:
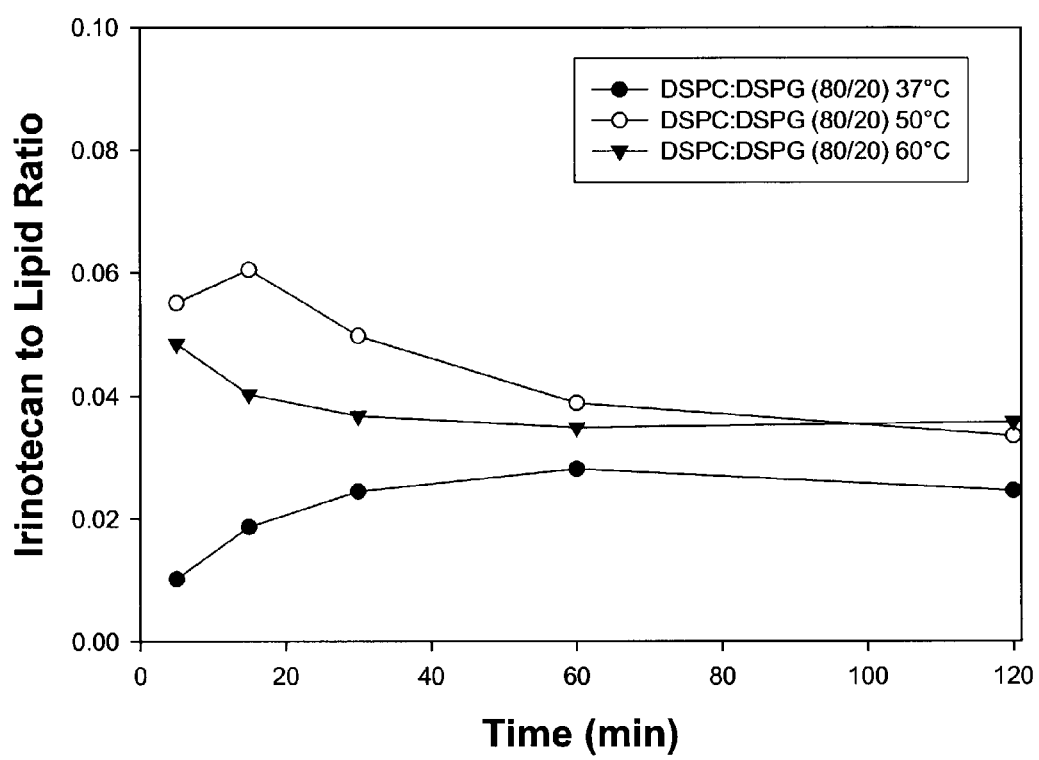
FIG. 18: a graph showing loading of irinotecan into DSPC/DSPG (80:20 mol ratio) liposomes in response to encapsulated $CUSO_4$ a 37° C. (●), 50° C. (○) and 60° C. (▼). The external solution of the liposome was buffer exchanged into saline and further exchanged into 300 mM sucrose, 20 mM HEPES, pH 7.4 (no external EDTA) before loading.

Metal-based loading of drug in the presence and absence of metal ions on the external surface of phosphatidylglycerol containing liposomes was examined and results are depicted in FIGS. 17 and 18.

Liposomes composed of DSPC/DSPG (80:20 mole ratio) were prepared following the procedures as described in Example 1. DSPC and DSPG lipids were dissolved in chloroform and chloroform/methanol/water (50:10:1 v/v), respectively. The lipids were then combined in appropriate amounts for each formulation. Solvent was removed under a steady stream of $N_2$ gas while maintaining the temperature at 70° C. and put under vacuum for 5 minutes. The resulting lipid films were redissolved in chloroform to further remove any methanol or water and then solvent was removed as before and dried under vacuum to remove any residual solvent. The samples were subsequently rehydrated in 150 mM $CUSO_4$, pH 7.4 (pH adjusted with TEA) and the resulting MLVs were extruded at 70° C. Liposome samples were either run down a 15 mL Chelex-100™ (BioRad) column equilibrated with 150 mM NaCl at 0.5 mL/min or buffer exchanged into saline and further exchanged into 300 mM sucrose, 20 mM HEPES, pH 7.4 using tangential flow. Liposomes that were passed through the Chelex-100™ column were subsequently exchanged into 300 mM sucrose, 20 mM HEPES, pH 7.4 using tangential flow.

Both liposome preparations were then loaded at 37, 50 and 60° C. with irinotecan at a drug to lipid weight ratio of 0.1:1 as described above. Drug uptake was assayed using liquid scintillation counting to determine lipid concentrations and absorbance at 370 nm to determine irinotecan concentrations after solubilization in detergent.

Results depicted in FIG. 17 reveal that loading of irinotecan into DSPC/DSPG (80:20 mole ratio) liposomes was enhanced when the liposome preparation was passed through a Chelex-100™ column to remove external metal ions. In contrast, results shown in FIG. 18 demonstrate that loading of irinotecan into liposomes exchanged into a solution not containing a chelating agent loaded at a reduced rate. Although not wishing to be bound by any particular theory, removal of metal ions associated with the negatively charged liposomal surface by complexing the ions with a chelating agent may reduce metal-drug interactions on the outer surface of the membrane thereby increasing the amount of free drug that may cross the membrane to become entrapped in the internal compartment of the liposome.

Example 15

Methods for the Removal of Metal Ions From the External Solution of Liposomes

Copper-based loading of irinotecan into DSPC/DSPG (80:20 mole ratio) liposomes was investigated after removal of $Cu^{2+}$ from the external solution using two different techniques both reliant on chelation of the external metal. The first technique involved removal of the copper by passage through a Chelex™ column and the second technique involved exchanging the liposomes into a buffer containing EDTA.

DSPC/DSPG (80:20 mole ratio) were prepared as in Example 14, except that samples were rehydrated in 150 mM copper gluconate, pH 7.4 (pH adjusted with TEA). External copper was removed by: i) passage through a 15 mL Chelex-100 column equilibrated in 300 mM sucrose, 20 mM HEPES, pH 7.4; or ii) by buffer exchange into saline and then into 300 mM sucrose, 20 mM HEPES, 30 mM EDTA, pH 7.4 (SHE buffer) using tangential flow.

Both liposome preparations were then loaded at 37, 50 and 60° C. with irinotecan at a drug to lipid weight ratio of 0.1:1 as described in Example 14. Aliquots (100 µL) were removed at various time points after initiation of loading and applied to a Sephadex G-50 spin column. The samples were then solubilized in detergent and drug and lipid quantitation was performed as previously described in Example 14.

Figure 19:
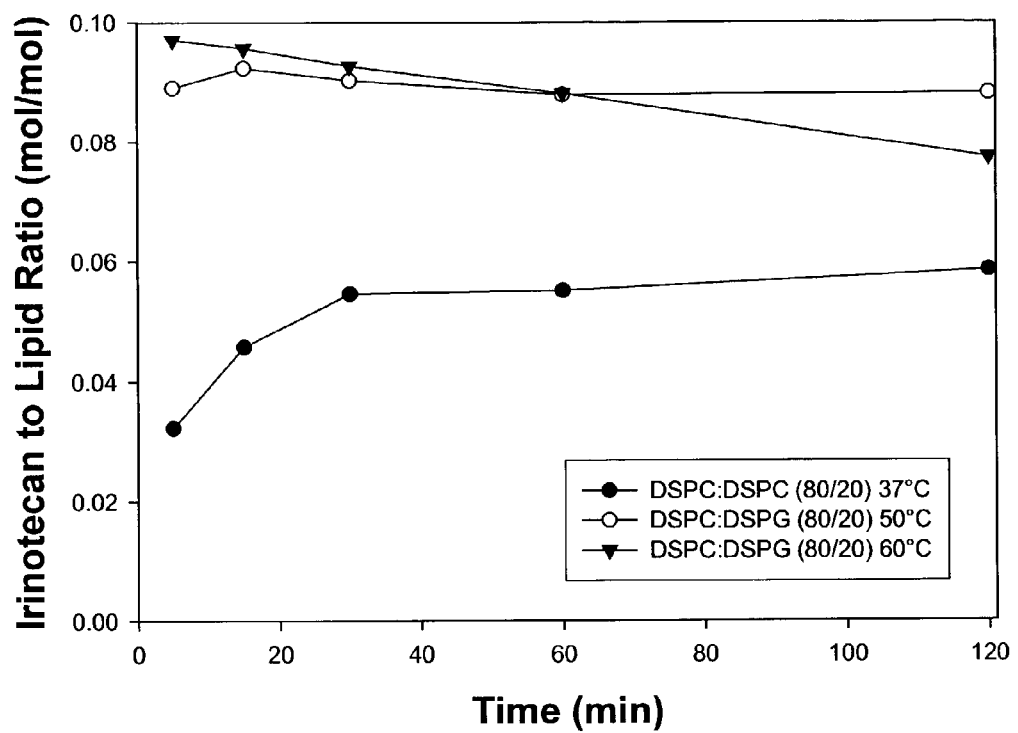
FIG. 19: a graph showing loading of irinotecan into DSPC/DSPG (80:20 mol ratio) liposomes in response to encapsulated copper gluconate after buffer exchange of the external solution into 300 mM sucrose, 20 mM HEPES, 30 mM EDTA, pH 7.4. Loading was carried out by incubation at 37° C. (●), 50° C. (○) and 60° C. (▼).
Figure 20:
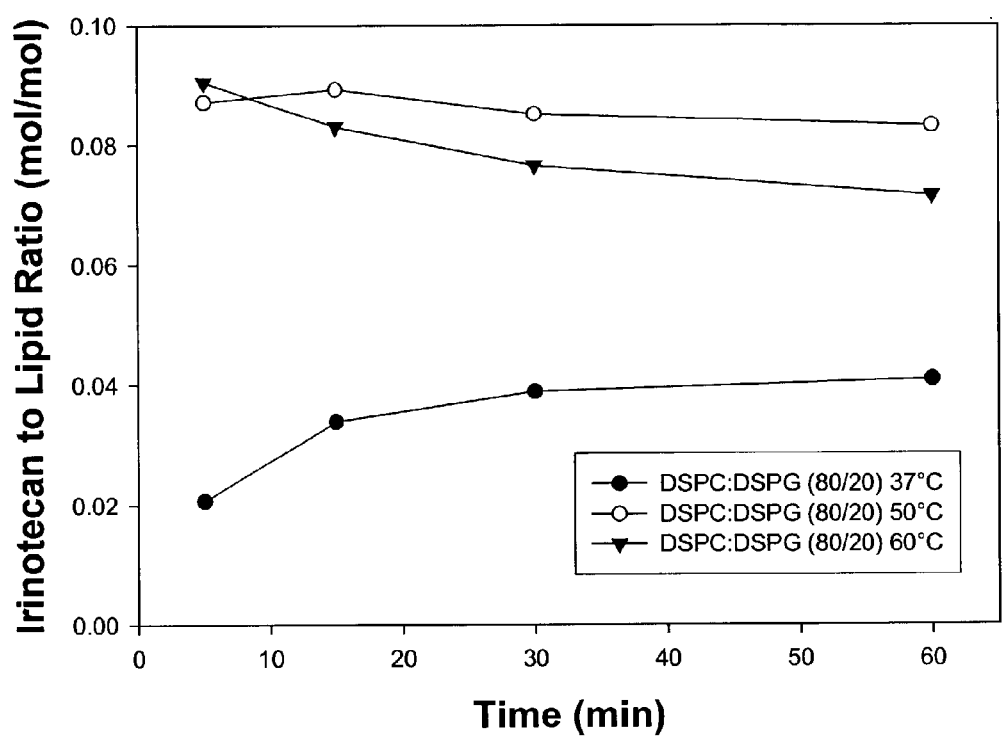
FIG. 20: a graph showing loading of irinotecan into DSPC/DSPG (80:20 mol ratio) liposomes in response to encapsulated copper gluconate after passage of the liposome preparations through a Chelex-100™ column equilibrated with 300 mM sucrose, 20 mM HEPES, pH 7.4. Loading of irinotecan was carried out by incubation at 37° C. (●), 50° C. (○) and 60° C. (▼).

Meta-based loading of irinotecan after removal of external metal by passage through a chelation column (FIG. 20) is comparable to loading after exchanging the liposomes into an EDTA-containing solution (FIG. 19). These results thus demonstrate that various means may be employed to remove exterior metal ions from negatively charged membranes without considerably affecting loading efficiency.

Example 16

Pharmacokinetics of Phosphatidylglycerol-containing Liposomes Co-loaded with Daunorubicin and Carboplatin The retention of daunorubicin and carboplatin co-encapsulated in PG-containing liposomes was investigated by passive loading of carboplatin followed by metal loading of daunorubicin.

Daunorubicin and carboplatin were encapsulated in DSPC/DSPG (80:20 mole ratio), DSPC/SM/DSPG (75:5:20 mole ratio) and DSPC/SM/DSPG (70:10:20 mole ratio) liposomes. The liposomes were prepared following the procedures as described in preceding examples. DSPG was dissolved in a solution of 50:10:1 chloroform/methanol/water (v/v) and the radioactive marker 14C—CHE was added to the preparation to quantify lipid. The lipid films were rehydrated in 150 mM $CuSO_4$, 20 mM histidine, pH 7.4 containing 80 mg/mL carboplatin (with 4% DMSO to improve carboplatin solubility). After extrusion, samples were centrifuged to remove unencapsulated carboplatin. Liposomes exchanged into SHE buffer were loaded with $^3$H-daunorubicin. Mice were administered liposomes at a dose of 100 mg/kg lipid. Liquid scintillation counting was used to quantitate daunorubicin and lipid. Plasma carboplatin levels were determined by atomic absorption.

Figure 21:
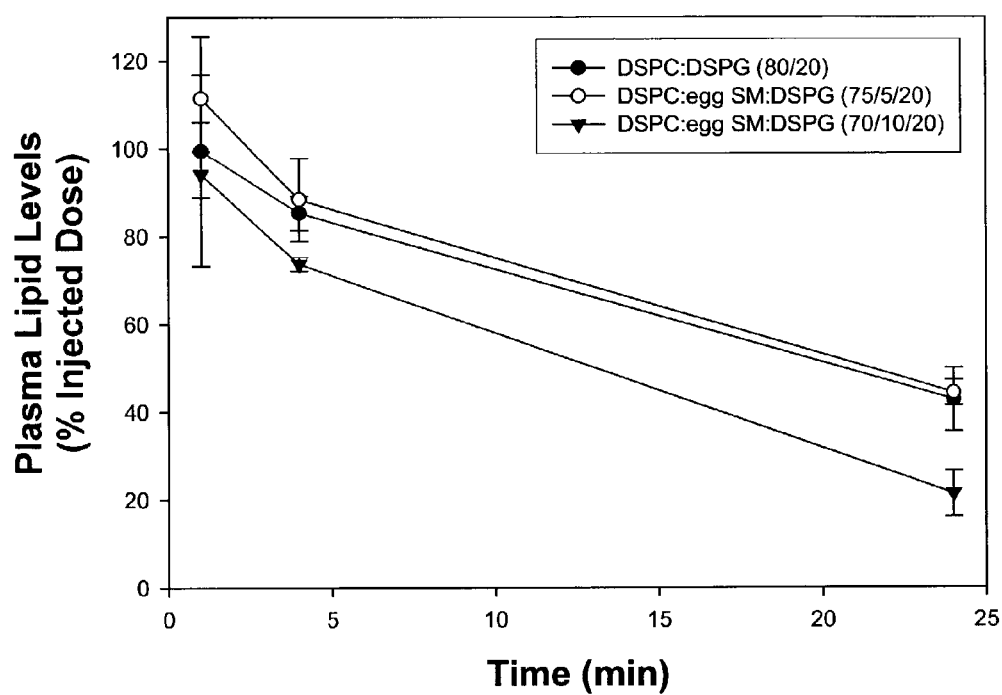
FIG. 21: a graph showing plasma lipid levels of DSPC/DSPG (80:20 mol ratio), DSPC/SM/DSPG (75:5:20 mol ratio) and DSPC/SM/DSPG (70:10:20 mol ratio) liposomes co-loaded with daunorubicin and carboplatin represented by ●, ○, and ▼ respectively. Carboplatin was passively entrapped and daunorubicin was actively loaded in response to encapsulated $CuSO_4$.
Figure 22:
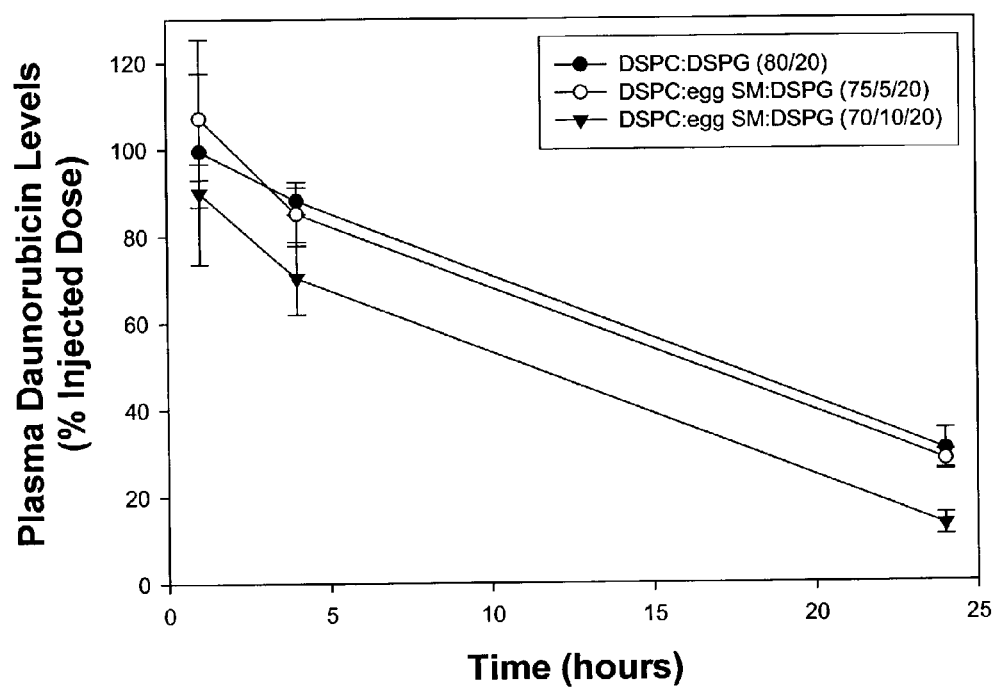
FIG. 22: a graph showing plasma daunorubicin levels of DSPC/DSPG (80:20 mol ratio), DSPC/SM/DSPG (75:5:20 mol ratio) and DSPC/SM/DSPG (70:10:20 mol ratio) liposomes co-loaded with daunorubicin and carboplatin represented by ●, ○, and ▼ respectively. Carboplatin was passively entrapped and daunorubicin was actively loaded in response to encapsulated $CuSO_4$.
Figure 23:
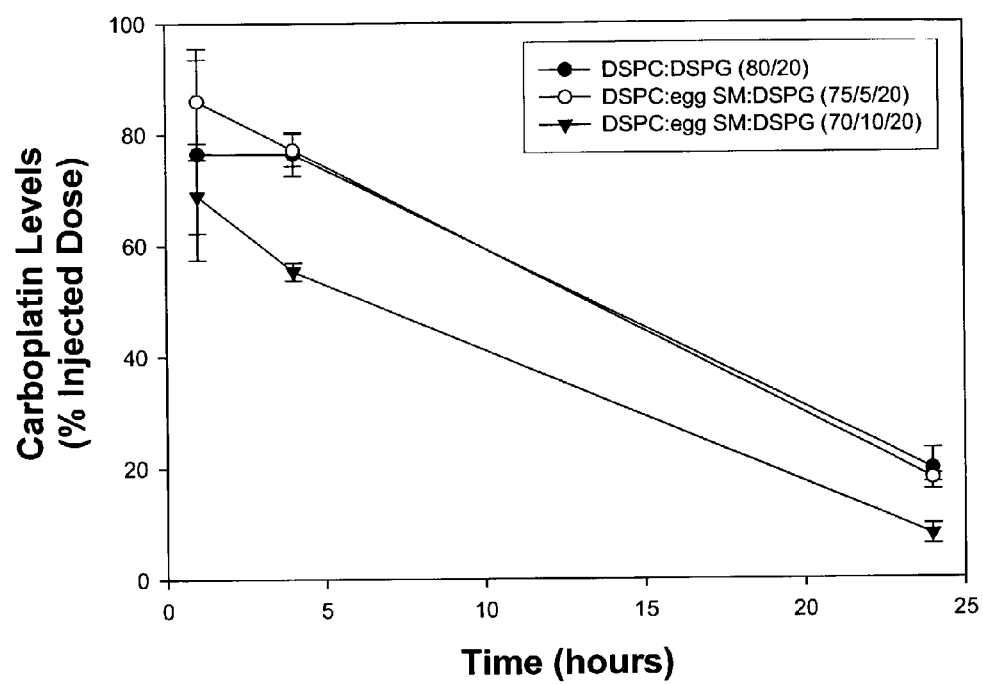
FIG. 23: a graph showing plasma carboplatin levels of DSPC/DSPG (80:20 mol ratio), DSPC/SM/DSPG (75:5:20 mol ratio) and DSPC/SM/DSPG (70:10:20 mol ratio) liposomes co-loaded with daunorubicin and carboplatin represented by ●, ○, and ▼ respectively. Carboplatin was passively entrapped and daunorubicin was actively loaded in response to encapsulated $CuSO_4$.

Results in FIG. 21 indicate that dual loaded DSPC/DSPG (80:20 mole ratio), DSPC/SM/DSPG (75:5:20 mole ratio) and DSPC/SM/DSPG (70:10:20 mole ratio) liposomes display enhanced plasma lipid levels at various time points after intravenous administration, although liposomes prepared with 10 mol % sphingomyelin exhibited lower lipid levels in relation to liposomes with 5 mol % sphingomyelin. The liposomes effectively altered the pharmacokinetics of the drug as demonstrated by the high levels daunorubicin and carboplatin remaining in the blood compartment after administration (see FIGS. 22 and 23). Liposomes prepared with DSPC/DSPG (80:20 mole ratio) and DSPC/SM/DSPG (75:5:20 mole ratio) exhibited the highest daunorubicin and carboplatin levels in relation to DSPC/SM/DSPG (70:10:20 mole ratio) liposomes.

Although the foregoing invention has been described in some detail by way of illustration and examples for purposes of clarity and understanding, it will be readily apparent to those of skill in the art in light of the teachings of this invention that changes and modification may be made thereto without departing from the spirit of scope of the appended claims. All patents, patent applications and publications referred to herein are incorporated herein by reference.

We claim:

1. A method of loading at least one therapeutic agent into a liposome in a liposome composition, the method comprising:
   i) providing a composition comprising liposomes, said liposomes lacking an ionophore, in an external solution, the liposomes containing an internal solution comprising encapsulated copper ions;
   ii) adding at least one therapeutic agent to the external solution; and
   iii) maintaining the agent in the external solution for sufficient time to load the agent into the liposomes.

2. The method of claim 1, wherein the internal solution comprises a copper compatible solution.

3. The method of claim 1, wherein the external solution and external surfaces of the liposome contain substantially no uncomplexed copper ions.

4. The method of claim 3, wherein the external solution comprises a copper chelating agent.

5. The method of claim 3, wherein uncomplexed copper ions are removed, from the external solution prior to step (ii) by chromatography or by extensive solution exchange or dialysis.

6. The method of claim 1, wherein the internal solution and the external solution have substantially the same pH.

7. The method of claim 1, wherein the liposomes have less than 20 mol % cholesterol.

8. The method of claim 1, wherein the pH of the internal solution is in the range of about 6.0 to about 8.5.

9. The method of claim 1, wherein the liposomes comprise one or more lipids that are negatively charged at physiological pH.

10. The method of claim 9, wherein the one or more negatively charged lipids are selected from PG and PI.

11. The method of claim 1, wherein a second therapeutic agent is loaded by means of a transmembrane gradient established with an ionophore supplied to the liposomes after step (iii).

12. A method of loading at least one therapeutic agent into a liposome in a liposome composition, the method comprising:

i) providing a composition comprising liposomes in an external solution, the liposomes containing an internal solution comprising encapsulated copper ions;

ii) adding at least one therapeutic agent to the external solution; and iii) maintaining the agent in the external solution for sufficient time to load the agent into the liposomes, and wherein the liposomes do not at any time during said loading comprise an ionophore.

13. A method of loading at least one therapeutic agent into a liposome in a liposome composition, the method comprising:

i) providing a composition comprising liposomes in an external solution, the liposomes containing an internal solution comprising encapsulated copper ions;

ii) adding at least one therapeutic agent to the external solution; and iii) maintaining the agent in the external solution for sufficient time to load the agent into the liposomes, and wherein said loading is conducted in the absence of ionophore.

* * * * *